United States Patent
Lei et al.

(10) Patent No.: US 11,162,859 B2
(45) Date of Patent: Nov. 2, 2021

(54) SYSTEM AND METHOD FOR MEASURING PRESSURE OF FLUID FLOW

(71) Applicant: Haemonetics Corporation, Boston, MA (US)

(72) Inventors: Ming Lei, Sharon, MA (US); Matthew Murphy, Marshfield, MA (US)

(73) Assignee: Haemonetics Corporation, Boston, MA (US)

(*) Notice: Subject to any disclaimer, the term of this patent is extended or adjusted under 35 U.S.C. 154(b) by 133 days.

(21) Appl. No.: 15/745,882

(22) PCT Filed: Jul. 20, 2016

(86) PCT No.: PCT/US2016/043055
§ 371 (c)(1),
(2) Date: Jan. 18, 2018

(87) PCT Pub. No.: WO2017/015322
PCT Pub. Date: Jan. 26, 2017

(65) Prior Publication Data
US 2018/0202881 A1    Jul. 19, 2018

Related U.S. Application Data

(60) Provisional application No. 62/194,436, filed on Jul. 20, 2015.

(51) Int. Cl.
*G01L 7/08*      (2006.01)
*G01L 19/06*     (2006.01)
(Continued)

(52) U.S. Cl.
CPC ............ *G01L 7/082* (2013.01); *A61B 5/6866* (2013.01); *A61M 1/367* (2013.01);
(Continued)

(58) Field of Classification Search
CPC ... G01L 7/082; G01L 19/003; G01L 19/0023; G01L 19/0645; A61B 5/6866;
(Continued)

(56) References Cited

U.S. PATENT DOCUMENTS

| 4,190,426 A | * | 2/1980 | Ruschke | ................. A61M 5/36 96/6 |
| 4,658,651 A | * | 4/1987 | Le | ......................... G01L 1/2293 29/621.1 |

(Continued)

FOREIGN PATENT DOCUMENTS

| CN | 104069558 A | 10/2014 |
| CN | 104363935 A | 2/2015 |

(Continued)

OTHER PUBLICATIONS

USPTO as the International Searching Authority, Authorized Officer: Shane Thomas, International Search Report and Written Opinion of the International Searching Authority, PCT/US16/43055, dated Oct. 7, 2016, 18 pages.

(Continued)

*Primary Examiner* — Nathaniel T Woodward
(74) *Attorney, Agent, or Firm* — Sunstein LLP

(57) ABSTRACT

An apparatus for measuring pressure within a fluid path includes a housing defining the structure of the apparatus. The housing includes a fluid path that extends through the housing and allows a fluid to pass through the housing. The apparatus also includes a first volume chamber that is in fluid communication with the fluid path and has a first volume chamber opening, and a second volume chamber with a second volume chamber opening that is less than the first volume chamber opening. A diaphragm separates the first volume chamber from the second volume chamber and fluidly disconnects the second volume chamber from the fluid path. The diaphragm deforms based upon the pressure (Continued)

within the fluid path. The apparatus also includes an interface that is connectable to a pressure sensor, and the second volume chamber is in fluid communication with the interface.

25 Claims, 12 Drawing Sheets

(51) Int. Cl.
    *A61M 1/36*       (2006.01)
    *G01L 19/00*      (2006.01)
    *A61B 5/00*       (2006.01)
    *A61B 5/021*      (2006.01)

(52) U.S. Cl.
    CPC ......... *A61M 1/3641* (2014.02); *G01L 19/003* (2013.01); *G01L 19/0023* (2013.01); *G01L 19/0645* (2013.01); *A61B 5/021* (2013.01); *A61M 2230/30* (2013.01)

(58) Field of Classification Search
    CPC ..... A61B 5/021; A61M 1/3641; A61M 1/367; A61M 2230/30
    USPC .......................................................... 73/730
    See application file for complete search history.

(56) References Cited

U.S. PATENT DOCUMENTS

| | | | | |
|---|---|---|---|---|
| 4,817,629 A | * | 4/1989 | Davis | A61B 5/0215 600/488 |
| 4,947,856 A | | 8/1990 | Beard | |
| 5,439,021 A | * | 8/1995 | Burlage | F15B 13/0405 137/269 |
| 2004/0050168 A1 | | 3/2004 | Uberreiter | |
| 2005/0139010 A1 | * | 6/2005 | Wang | G01L 9/0072 73/718 |
| 2009/0078054 A1 | | 3/2009 | Romo | |
| 2011/0250585 A1 | | 10/2011 | Ingber et al. | |
| 2012/0130338 A1 | | 5/2012 | Schnell et al. | |
| 2014/0052009 A1 | | 2/2014 | Nystrom | |

FOREIGN PATENT DOCUMENTS

| | | |
|---|---|---|
| CN | 104582753 A | 4/2015 |
| JP | H09-24026 | 1/1997 |
| WO | WO 2007/085993 | 8/2007 |
| WO | WO 2014/028103 | 2/2014 |
| WO | WO 2014093846 A1 | 6/2014 |

OTHER PUBLICATIONS

European Patent Office, Extended European Search Report, application No. 16828437.0, 10 pages, dated Jan. 16, 2019.
China National Intellectual Property Administration, Office Action dated Sep. 3, 2019 (application No. 201680050041.9) (with English translation).
Japanese Patent Office, Office Action dated Jun. 30, 2020 (application No. 2018-502013).
Japanese Patent Office, Office Action dated Jun. 30, 2020 (application No. 2018-502013) (English translation).

* cited by examiner

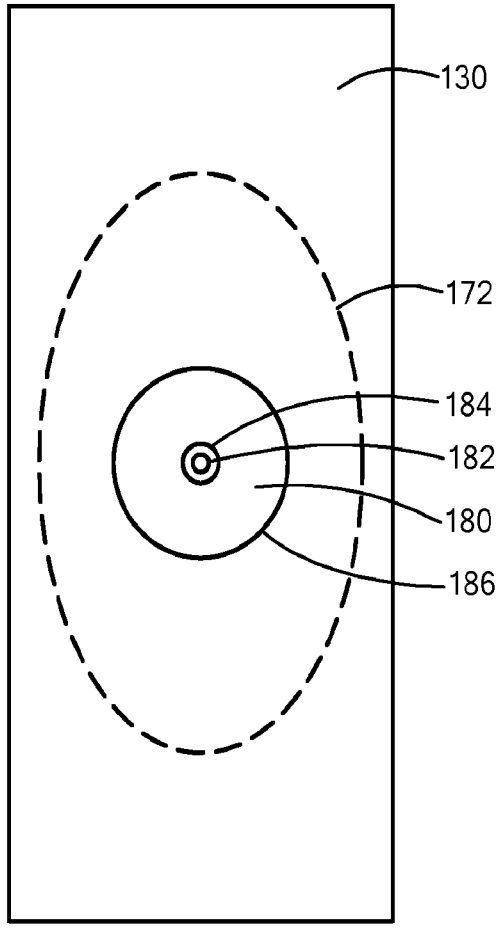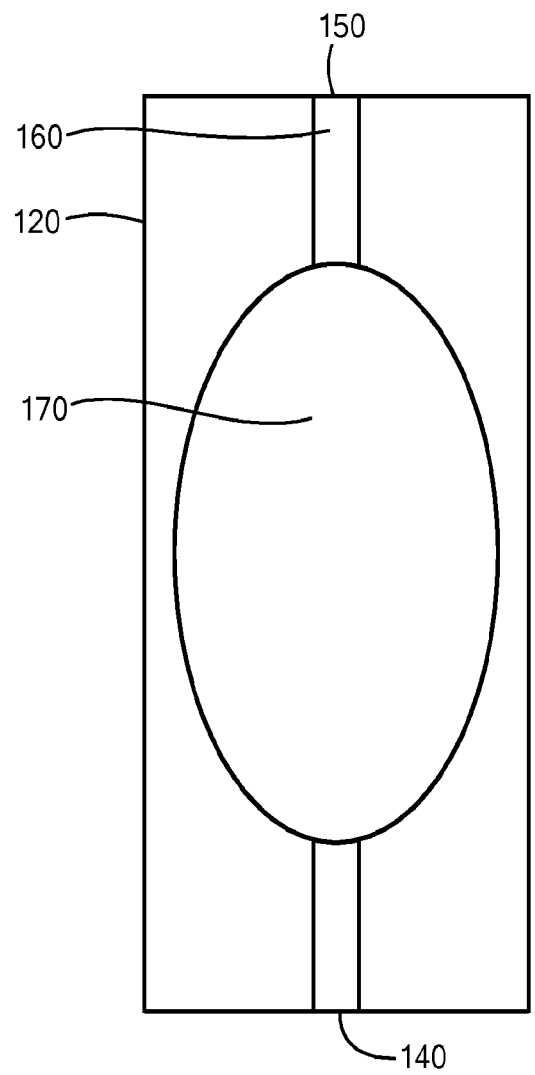
*Figure 3*  *Figure 4*

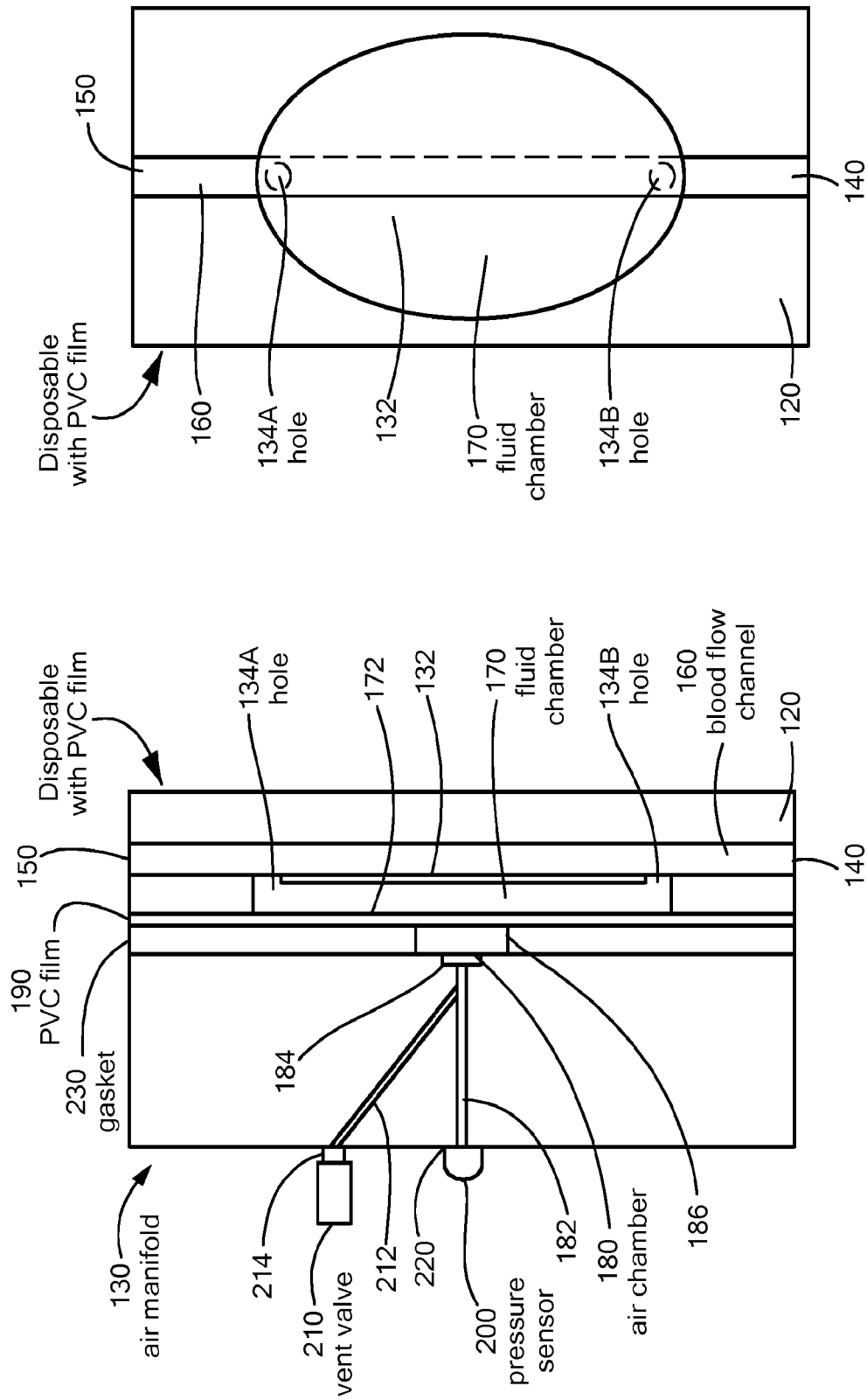

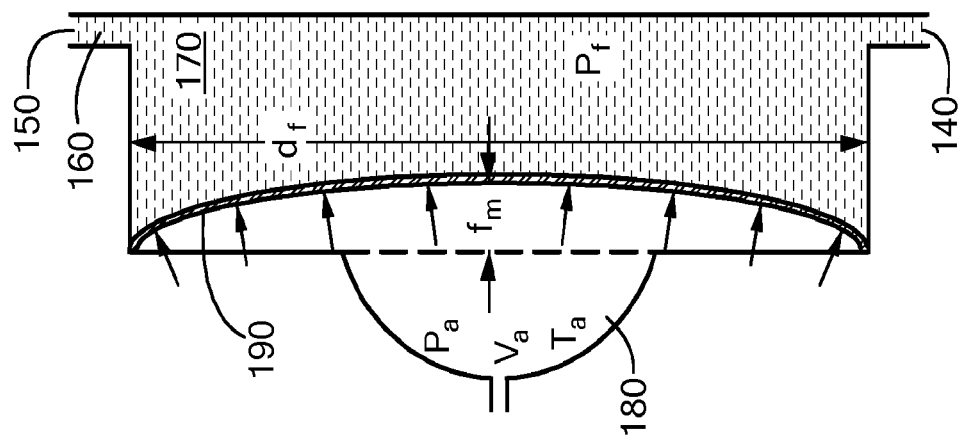
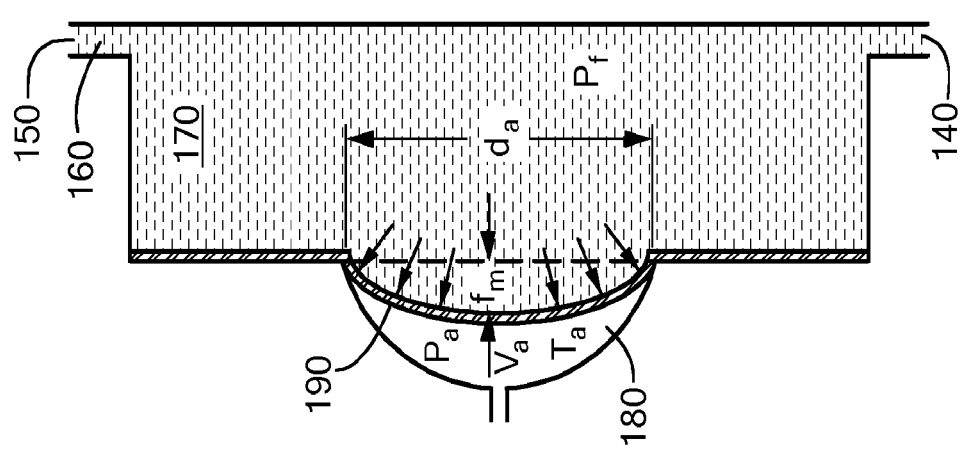
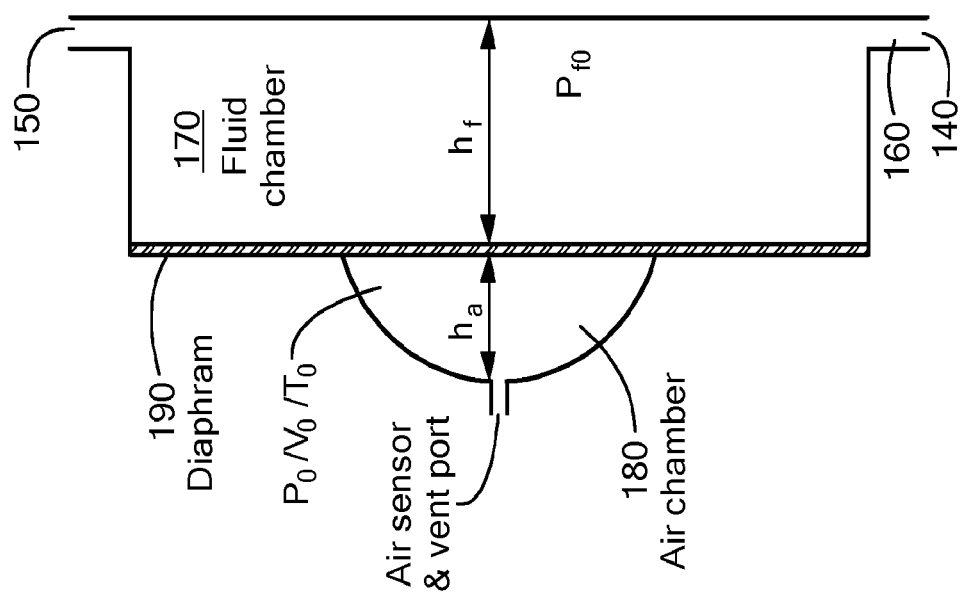

SYSTEM AND METHOD FOR MEASURING PRESSURE OF FLUID FLOW

PRIORITY

This patent application claims priority from U.S. Provisional Patent Application No. 62/194,436, filed Jul. 20, 2015, entitled, "System and Method For Measuring Pressure of Fluid Flow," and naming Ming Lei and Matthew J. Murphy as inventors, the disclosure of which is incorporated herein, in its entirety, by reference.

TECHNICAL FIELD

The present invention relates to fluid flow systems such as blood processing systems, and more particularly to pressure monitoring within fluid flow systems.

BACKGROUND ART

Many current blood systems (e.g., apheresis systems) process a number of fluids and have complex fluid path arrangements. During blood processing, the pressure within the fluid lines is critical to patient safety and system performance and efficiency. To that end, blood processing systems typically monitor the pressure within some or all of the fluid lines (especially the draw and return lines). In an apheresis device, for example, the donor pressure may be monitored to ensure that it does not go above or below a threshold during withdrawal of whole blood and return of blood components. A few pressure monitoring solutions have been implemented but each has significant drawbacks.

Some prior art systems have a monitoring line connected to the fluid line. The monitoring line may contain a 0.2 micron filter and may be manually connected to a pressure transducer by way of a tapered luer fitting. As the pressure within the fluid line increases, the fluid compresses a column of air trapped in the monitoring line between the flowing fluid and the transducer. The pressure transducer then detects the change in pressure. The system can detect a drop in pressure in a similar manner. Although this approach has been proven effective, it has several drawbacks. First, these designs require the operator to connect to each transducer manually, making it prone to bad connections. If the connection is not air-tight, fluid may force the air out of the column and wet the transducer protector. If this happens, the sensor/transducer will no longer function. Additionally, when measuring large negative pressures, air in the pressure tubing may get into the blood line and form air bubbles in the blood, which is very harmful to patients or donors if not removed. Conversely, during large positive pressures, the blood may reach the filter, causing the pressure measurement system to fail. Furthermore, repeated pressure fluctuations may introduce extra air bubbles into the pressure tubing, which negatively impacts the pressure measurement accuracy Other prior art systems have taken a different approach. These systems have a flexible membrane (silicone, for example) within the fluid path. The membrane is in contact with the fluid on one side and a transducer on the other. Increases in pressure within the fluid line create a pressure on the transducer through the flexible membrane. However, these systems have difficulty accurately and reproducibly measuring negative pressures.

SUMMARY OF THE INVENTION

In a first embodiment of the invention there is provided an apparatus for measuring pressure within a fluid path. The apparatus includes a housing, a first volume chamber, and a second volume chamber. The housing defines the structure of the apparatus and may have a fluid path that, at least partially, extends through the housing and allows a fluid to pass through the housing. The first volume chamber may be in fluid communication with the fluid path and may have a first volume chamber opening. The second volume chamber may have a second volume chamber opening that is smaller than the first volume chamber opening. The apparatus may also have a diaphragm that separates the first volume chamber from the second volume chamber and fluidly disconnects the second volume chamber from the fluid path. The diaphragm may deform based upon the pressure within the fluid path. The second volume chamber may be in fluid communication with an interface that is connectable to a pressure sensor.

In some embodiments, the housing may include a first portion and a second portion. The first volume chamber may be located within the first portion, the second volume chamber may be located in the second portion, and the diaphragm may be located between the first and second portion. The second portion may be an air manifold, and/or the first portion may be disposable and disconnected from the second portion. Additionally, a gasket may extend between the first and second portion to prevent air leakage when the first and second portions are coupled. The gasket may have an opening that defines at least a portion of the second volume chamber. The diaphragm may be ultrasonically welded to the first portion to seal the first volume chamber. The fluid path may, at least partially, extend through the first portion of the housing. The housing may also have a vent port that is in fluid communication with the second volume chamber via a vent channel. The vent port and vent channel may allow the second volume chamber to vent as the diaphragm deforms. The apparatus may also include a vent valve located on the vent port.

The diaphragm may deform into the second volume chamber if the pressure within the fluid path is positive, and/or deform into the first volume chamber if the pressure within the fluid path is negative. In some embodiments, a wall of the second volume chamber may have a curved surface, and the diaphragm may deform to the curved surface at a maximum pressure within the fluid path. The housing may have an air path between the second volume chamber and the interface. Additionally or alternatively, the second volume chamber may have a recess located within a wall of the second volume chamber. The recess may prevent the diaphragm from occluding the air path. The housing may have a wall between the first volume chamber and the fluid path, and the wall may have one or more holes extending through it to fluidly connect the first volume chamber and the fluid path.

The apparatus may include a pressure sensor that is connectable to the interface and may measure the pressure within the fluid path. The first volume chamber may have a first volume and the second volume chamber may have a second volume. The second volume may be less than the first volume. A ratio of the size of the second volume chamber opening to the first volume chamber opening may be between 4:1 and 9:1. The first volume chamber may be a liquid chamber, and the first volume may fill with at least a portion of the fluid passing through the fluid path. The second volume chamber may be an air chamber.

In accordance with additional embodiments, a method for monitoring pressure within a fluid path includes fluidly connecting a pressure monitoring device to a fluid flow system (e.g., a blood processing system) and flowing a fluid through the pressure monitoring device (e.g., via a fluid path in the device). The pressure monitoring device may include a housing, a first volume chamber, and a second volume chamber. The housing defines the structure of the apparatus and has a fluid path at least partially extending through the housing. The fluid path allows the fluid to pass through the housing. The first volume chamber is in fluid communication with the fluid path and has a first volume chamber opening. The second volume chamber has a second volume chamber opening that is smaller than the first volume chamber opening. The device may also include a diaphragm and an interface. The diaphragm separates the first volume chamber from the second volume chamber and fluidly disconnects the second volume chamber from the fluid path. The interface may connect to a pressure sensor, and the second volume chamber may be in fluid communication with the interface.

When the fluid flows through the pressure monitoring device via the fluid path, a pressure is created within the fluid path. A negative pressure within the fluid path causes the diaphragm to deform into the first volume chamber, and a positive pressure within the fluid path causes the diaphragm to deform into the second volume chamber and compress the second volume. The method may then measure the pressure within the fluid path using a pressure monitoring device. For example, the pressure within the fluid path may be a function of an amount of compression or expansion of the second volume.

The housing may include a first portion in which the first volume chamber is located and a second portion (e.g., an air manifold) in which the second volume chamber is located. The diaphragm may be located between the first and second portion. The first portion may be disposable and may be disconnected from the second portion. The device may also have a gasket that extends between the first and second portion, and prevents air leakage when the first and second portions are coupled. The gasket may have an opening through it that defines at least a portion of the second volume chamber. The fluid path may extend through the first portion of the housing, and the diaphragm may be ultrasonically welded to the first portion.

In some embodiments, the housing may include a vent port in fluid communication with the second volume chamber via a vent channel. The vent port and vent channel may allow the second volume chamber to vent as the diaphragm deforms. The device may have a vent valve located on the vent port. A wall of the second volume chamber may have a curved surface, and the diaphragm may deform to the curved surface at a maximum pressure within the fluid path. The housing may have an air path between the second volume chamber and the interface. The second volume chamber may have a recess located within a wall of the second volume chamber to prevent the diaphragm from occluding the air path.

In additional embodiments, the housing may include a wall between the first volume chamber and the fluid path. The wall may have one or more holes extending through it to fluidly connect the first volume chamber and the fluid path. The wall may prevent liquid from the fluid path from entering the first volume chamber. The first volume chamber may have a first volume and the second volume chamber may have a second volume that is less than the first volume. The first volume chamber may be a liquid chamber, and the first volume may fill with liquid passing through the fluid path. The second volume chamber may be an air chamber, and/or the method may include connecting the pressure monitoring device to the interface.

In an additional embodiment of the invention there is provided an apparatus for measuring pressure within a fluid path. The apparatus may include a housing, a first volume chamber, and a second volume chamber. The housing may define the structure of the apparatus and have a fluid path that at least partially extends through the housing. The fluid path may be configured to allow a fluid to pass through the housing. The first volume chamber may be in fluid communication with the fluid path and may have a first volume. The second volume chamber may have a second volume that is less than the first volume. The apparatus may also include a diaphragm and an interface connectable to a pressure sensor. The diaphragm may separate the first volume chamber from the second volume chamber, and fluidly disconnect the second volume chamber from the fluid path. The diaphragm may also be configured to deform based upon the pressure within the fluid path. The second volume chamber may be fluid communication with the interface.

In some embodiments, the housing may include a first portion and a second portion. In such embodiments, the first volume chamber may be located within the first portion, the second volume chamber may be located in the second portion, and the diaphragm may be located between the first and second portion. The second portion may be an air manifold, and the first portion may be a fluid housing. Additionally or alternatively, the first portion may be disposable and configured to be disconnected from the second portion. The apparatus may also include a gasket that extends between the first and second portions, and that is configured to prevent air leakage when the first and second portions are coupled. The gasket may include an opening that defines at least a portion of the second volume chamber. The fluid path may, at least partially, extend through the first portion of the housing, and the diaphragm may be ultrasonically welded to the first portion to seal the first volume chamber.

The housing may also include a vent port in fluid communication with the second volume chamber via a vent channel. The vent port and vent channel may be configured to allow the second volume chamber to vent as the diaphragm deforms. The apparatus may include a vent valve located on the vent port.

The diaphragm may deform into the second volume chamber if the pressure within the fluid path is positive, and/or deform into the first volume chamber if the pressure within the fluid path is negative. A wall of the second volume chamber may have a curved surface, and the diaphragm may deform to the curved surface at a maximum pressure within the fluid path. Additionally or alternatively, the housing (e.g., the first portion) may include a wall between the first volume chamber and the fluid path. The wall may have one or more holes extending through it to fluidly connect the first volume chamber and the fluid path. The wall may prevent liquid from entering the first volume chamber.

In some embodiments, the housing may include an air path between the second volume chamber and the interface. The second volume chamber may also include a recess located within a wall of the second volume chamber. The recess may prevent the diaphragm from occluding the air path. The apparatus may also include a pressure sensor that is connectable to the interface and configured to measure the pressure within the fluid path. The first volume chamber may include a first volume chamber opening and the second volume chamber may include a second volume chamber opening. The ratio of the size of the second volume chamber opening to the first volume chamber opening may be between 4:1 and 9:1. The depth of the fluid chamber may be larger than the maximum diaphragm deformation into the first chamber. The first volume chamber may be a liquid chamber, and may fill with at least a portion of the fluid passing through the fluid path. The second volume chamber may be an air chamber.

In accordance with additional embodiments, a method for monitoring pressure within a fluid path may include fluidly connecting a pressure monitoring device to a fluid flow system. The pressure monitoring device may include a housing, a first and second volume chamber, a diaphragm and an interface. The housing may define the structure of the apparatus and have a fluid path that, at least partially, extends through the housing, and allows a fluid to pass through the housing. The first volume chamber may be in fluid communication with the fluid path and have a first volume. The second volume chamber may have a second volume that is less than the first volume. The diaphragm may separate the first volume chamber from the second volume chamber and fluidly disconnect the second volume chamber from the fluid path. The interface may be connectable to a pressure sensor, and in fluid communication with second volume chamber.

The method may also include (1) flowing a fluid through the pressure monitoring device via the fluid path to create a pressure within the fluid path, and (2) measuring the pressure within the fluid path using a pressure monitoring device. For example, a negative pressure within the fluid path may cause the diaphragm to deform into the first volume chamber, and a positive pressure within the fluid path may cause the diaphragm to deform into the second volume chamber and compress the second volume. The pressure within the fluid path may be correlated to the amount of compression and/or expansion of the second volume. The method may also include connecting the pressure monitoring device to the interface. The fluid flow system may be a blood processing device.

BRIEF DESCRIPTION OF THE DRAWINGS

The foregoing features of the invention will be more readily understood by reference to the following detailed description, taken with reference to the accompanying drawings, in which:

FIG. 3 schematically shows a bottom view of an air manifold section of the pressure measurement device shown in FIG. 1, in accordance with some embodiments of the present invention.

FIG. 4 schematically shows a fluid flow section of the pressure measurement device shown in FIG. 1, in accordance with some embodiments of the present invention.

FIG. 8 schematically shows a cross-sectional view of an additional alternative pressure measurement device, in accordance with further embodiments of the present invention.

FIG. 9 schematically shows a fluid flow section of the additional alternative pressure measurement device shown in FIG. 8, in accordance with some embodiments of the present invention.

FIGS. 19A-19C schematically show a cross-section of an exemplary pressure monitoring device during use, in accordance with various embodiments of the present invention.

DETAILED DESCRIPTION OF SPECIFIC EMBODIMENTS

Figure 1:
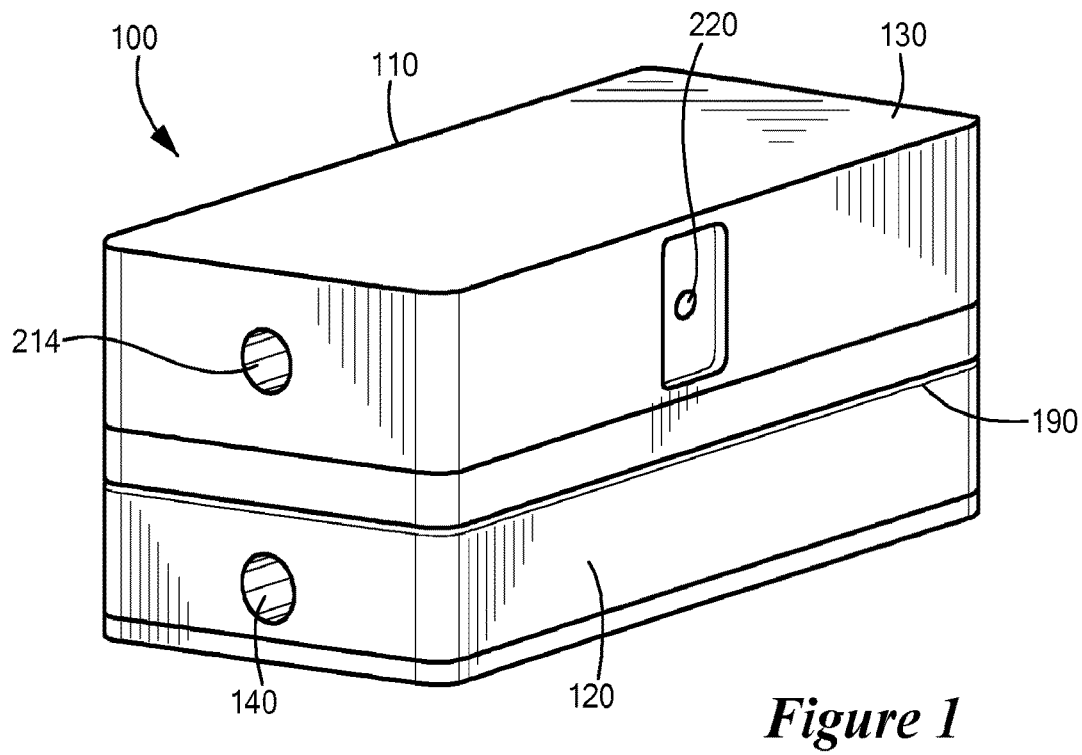
FIG. 1 schematically shows a pressure measurement device for measuring the pressure within a fluid path, in accordance with embodiments of the present invention.

FIG. 1 schematically shows a pressure measurement device 100 in accordance with various embodiments of the present invention. The device 100 includes a housing 110 that defines the structure of the device 100. The housing 110 may be a single piece or a multi-piece structure. For example, the housing 110 may have a first/bottom housing 120 and a second/top housing 130. The housing components may be assembled in a variety of ways including, but not limited to, clamping, adhesives, solvent bonding, thermal bonding, snap-fit, ultrasonic welding, and laser welding. Alternatively, the bottom and top housing 120/130 may be connected together (and, as discussed in greater detail below, subsequently disconnected) via a snap/clamp mechanism that allows a user to connect and disconnect the portions of the housing 110 as needed.

Figure 2:
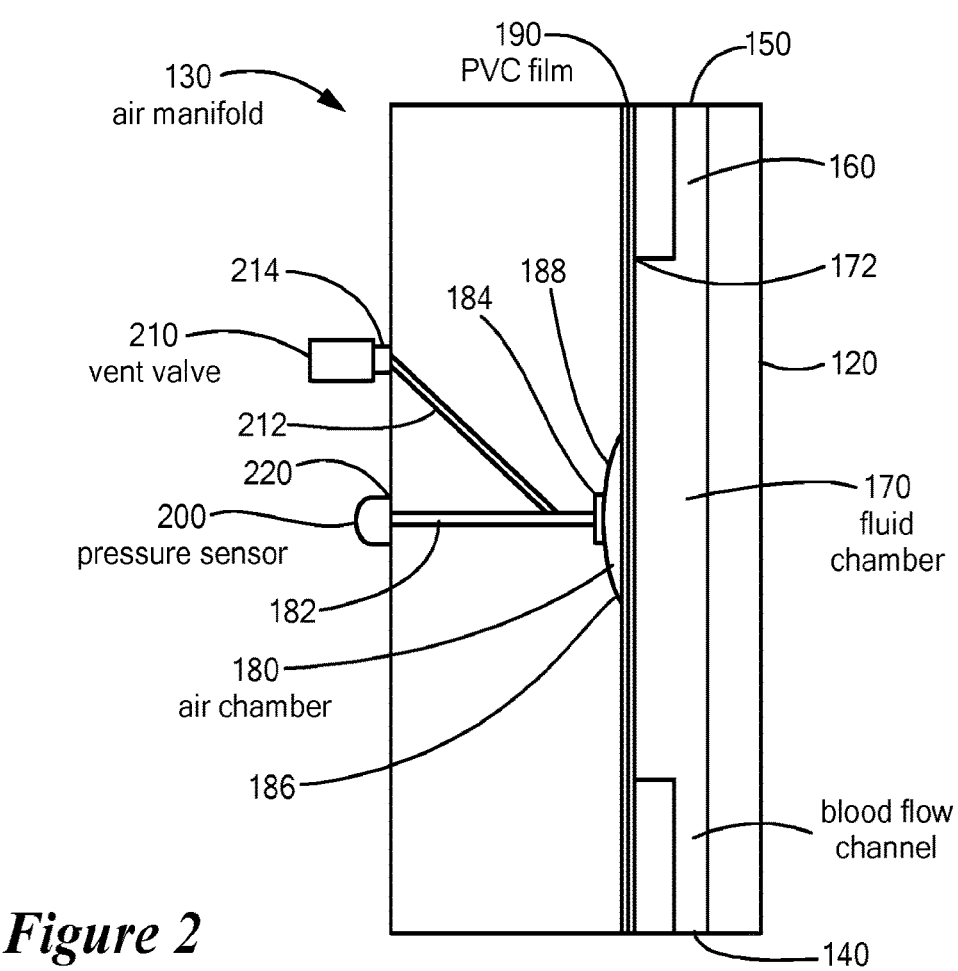
FIG. 2 schematically shows a cross-sectional view of the pressure measurement device shown in FIG. 1, in accordance with some embodiments of the present invention.

To facilitate fluid flow through the device 100, as shown in FIG. 2, the device 100 (e.g., the bottom housing 120, also referred to as the fluid housing below) may include an inlet port 140, an outlet port 150, and a fluid path 160 extending between the inlet 140 and outlet 150. When connected to a fluid flow/processing device (e.g., a blood processing device), fluid (e.g., blood or a blood component) may enter the pressure measurement device 100 via the inlet 140, flow through the fluid path 160, and exit the device 100 via the outlet 150. It should be noted that, although much of the discussion herein refers to port 140 as an inlet, and port 150 as an outlet, the ports 140/150 also may be respectively used as outlet and inlet ports. In other words, fluid may enter the device 100 via port 150, flow through the fluid path 160, and exit the device 100 via port 140.

As mentioned above, the device 100 may measure the pressure within the fluid path 160 as fluid (e.g., blood or blood components) is passing through the device 100. To that end, the fluid housing 120 may include a volume chamber (e.g., a fluid chamber 170) that is in fluid communication with the fluid path 160 such that fluid passing through the device 100 may enter the fluid chamber 170. In a similar manner, the top housing 130 (e.g., an air manifold/housing as discussed in greater detail below) may also include a volume chamber (e.g., an air chamber 180). To separate the fluid chamber 170 from the air chamber 180 and fluidly disconnect the air chamber 180 from the fluid path 160, the device 100 has a diaphragm 190 that extends between the housings 120/130. In some embodiments, the diaphragm 190 may be secured to and part of the fluid housing 120 and, as discussed in greater detail below, deform (e.g., into the fluid chamber 170 or air chamber 180 depending on whether the pressure is positive or negative) in response to the changes in pressure within the fluid path 160. The diaphragm 190 may be PVC film or other plastic material compatible with the fluid being sent through the device 100 and the fluid path 160.

As best shown in FIG. 2, the top housing 130 may include an interface 220 to which a pressure sensor/transducer 200 may be connected, and an air pathway 182 extending from the air chamber 180 to the interface 220. As discussed in greater detail below, the air pathway 182 allows pressure changes within the device 100/fluid path 160 to be translated to the pressure sensor/transducer 200. To prevent the air pathway 182 from becoming blocked by the diaphragm 190 as the diaphragm 190 deforms (e.g., in a max pressure scenario), the top housing 130 may include a recess 184 at the entrance to the air pathway 182. Furthermore to allow the air chamber 180 to vent in the presence of increased pressure and/or draw in air in the presence of a decreased pressure, the top housing 130 may also include a vent channel 212 and a vent port 214. To selectively control the flow in and out of the vent channel 212 via the vent port 214, the device 100 may include a vent valve 210 connected to the vent port 214.

It should be noted that, because the fluid passes through the fluid housing 120 and is separated from the top housing 130 via the diaphragm 190 (e.g., so that the fluid cannot enter the top housing 130 and the fluid chamber 170 is sealed), the bottom housing 120 essentially acts as a fluid housing (or blood flow unit in blood processing applications). Conversely, because the fluid never enters the top housing 130, the top housing 130 essentially acts as an air housing/manifold. Additionally, because the top housing 130 includes many of the more expensive components of the device 100 (e.g., the pressure sensor 200, the vent valve 210, etc.) and because the fluid never contacts any of the components of the top housing 130, the top housing 130 may be reusable and/or may be part of a larger device/machine (e.g., a blood processing device/system), whereas the fluid housing 120 may be disposable. Alternatively, in some applications and embodiments (e.g., in applications in which the fluid is corrosive, erosive, hazardous, or a biohazard), if a sufficiently inexpensive pressure sensor/transducer is used, the entire device 100 may be disposable.

As shown in FIGS. 2-4, the fluid chamber 170 and the opening 172 to the chamber 170 (e.g., approximately 2188 µL and 30×15 mm elliptic, 32×15 mm elliptic or 30×22 mm elliptic) may be considerably larger than the air chamber 180 and the opening 186 to the air chamber 180 (e.g., approximately 191 µL and 12 mm in diameter). In this manner, a larger membrane/diaphragm area can deflect toward the fluid/liquid chamber 170 than toward the air chamber 180. The ratio of fluid chamber opening 172 to the air chamber opening 186 may between 1.4:1 and 100:1. For example, the ratio of the fluid chamber opening 172 to the air chamber opening 186 may between 2.5:1 and 25:1 or between 4:1 and 9:1. Additionally, the openings 172/186 to the fluid and air chambers 170/180 may be any number of shapes (e.g., circular, elliptical, oval, square, rectangular etc.,) as long as the flow through the fluid path 160 and fluid chamber 170 is smooth and bubble free. Furthermore, the shape of the fluid chamber opening 172 need not be the same as the shape of the air chamber opening 186 (e.g., as shown in FIGS. 3 and 4, the air chamber opening 186 may be circular and the fluid chamber opening 172 may be elliptical).

By providing this unequal deformable membrane area, various embodiments of the present invention are able to accurately measure very large positive pressures and very large negative pressures (e.g., high vacuum), making the device 100 more robust than systems having equal chambers 170/180 and openings 172/186. For example, if the fluid chamber opening 172 is approximately 25.4 mm, and the air chamber opening 186 is 18 mm, the system/device 100 is able to measure positive pressures up to 700 mmHg with full scale ("FS") error less than 0.5% and negative pressures up to 400 mmHg with FS error less than 1%.

Furthermore, by utilizing the unequal chambers 170/180 and openings 172/186, some embodiments can tolerate certain non-perfect membrane conditions, temperature variation, and, possibly, some membrane property changes. For example, various embodiments of the system/device 100 can tolerate an initial membrane deflection equivalent to a deflection caused by a 0.5 mmHg cross-membrane pressure differential as well as a 15° C. temperature variation without sacrificing the device performance and with only a small reduction of full scale accuracy (e.g., for 700 mmHg positive pressure, FS error goes up to 1.5% and for 400 mmHg negative pressure, FS error increases to 1.8%). In contrast, prior art systems that utilize equal chambers 170/180 and openings 172/186 (e.g., 25.4 mm) can only measure 240 mmHg negative pressure with an estimated FS error 2.75%.

It should be noted that the each of the chambers 170/180, like their respective openings 172/186) can have any number of shapes (e.g., rectangular, circular, oval, square, etc.). Additionally or alternatively, in some embodiments, the wall 188 of the air chamber 180 (FIG. 2) may rounded/curved. In this manner, when the diaphragm 190 deforms into the air chamber 180, the diaphragm 190 may conform to the shape of the wall 188 (e.g., when under maximum pressure). However, in some embodiments, the depth of the curved surface 188 may be slightly larger than the expected maximum diaphragm deflection. Additionally, as discussed above, the recess 184 will prevent the diaphragm 190 from blocking the air path 182 when exposed to maximum pressure and when the diaphragm 190 has reached maximum deflection into the air chamber 180.

During use, the user/technician may connect the fluid pressure monitoring device 100 to a fluid flow system (e.g., a blood processing system). For example, the user/technician may connect the inlet 140 to a fluid source (e.g., a whole blood bag, a patient, a source of anticoagulant, a blood component bag, etc.) and the outlet 150 to fluid flow/processing equipment (e.g., blood processing equipment such as centrifuges, pumps, blood cleaning devices or other equipment that can be used to separate whole blood or otherwise process blood) or a patient/donor (if returning blood components to the donor). Once the inlet 140 and outlet 150 are connected, the user may begin to flow the fluid/liquid through the device (e.g., the user may begin the blood processing procedure).

As the fluid/liquid passes through the device 100, the fluid/liquid will enter the fluid chamber 170 and the pressure within the fluid path 160 will cause the diaphragm 190 to deform. In particular, if the fluid path 160 is under a positive pressure, the diaphragm will deform into the air chamber 180, translating the positive pressure within the fluid path 160 to the air chamber 180 and air path 182, and ultimately to the pressure sensor/transducer 200 connected to the interface 220 (e.g., by compressing the air within the air chamber 180). Conversely, when the fluid path 160 is under a negative pressure (e.g., a vacuum), the diaphragm 190 will deform into the fluid chamber 170, causing the air chamber 180 to expand and, thus, translate the negative pressure to the pressure sensor/transducer 200.

In some embodiments, as the pressure sensor/transducer 200 measures the pressure within the fluid path 160, the device 100 may transmit/send/communicate the pressure information to the fluid flow/processing system (e.g., the blood processing device). If the fluid flow/processing system is so equipped (e.g., with a microprocessor or other controller), the blood processing system may then increase, decrease, or maintain the fluid flow within the fluid path 160 based upon the pressure measured by the pressure monitoring device 100.

Figure 6:
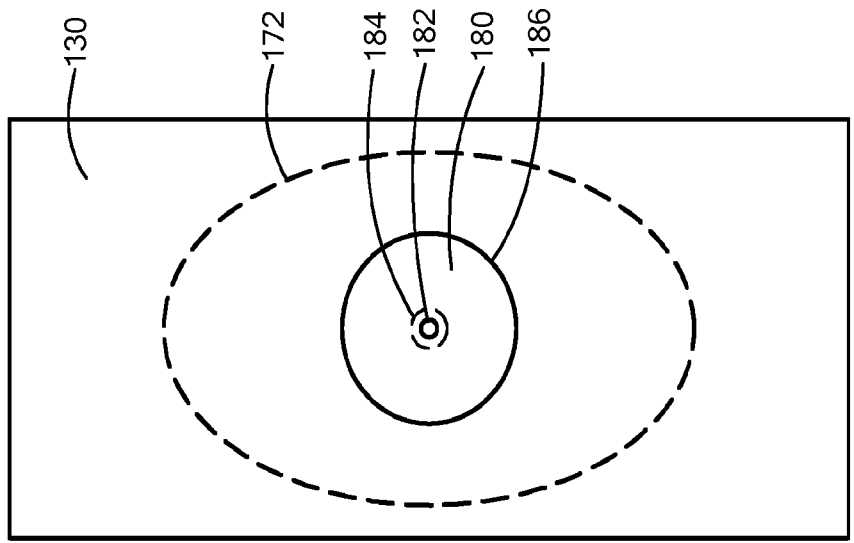
FIG. 6 schematically shows a bottom view of an air manifold section of the alternative pressure measurement device shown in FIG. 5, in accordance with some embodiments of the present invention.
Figure 5:
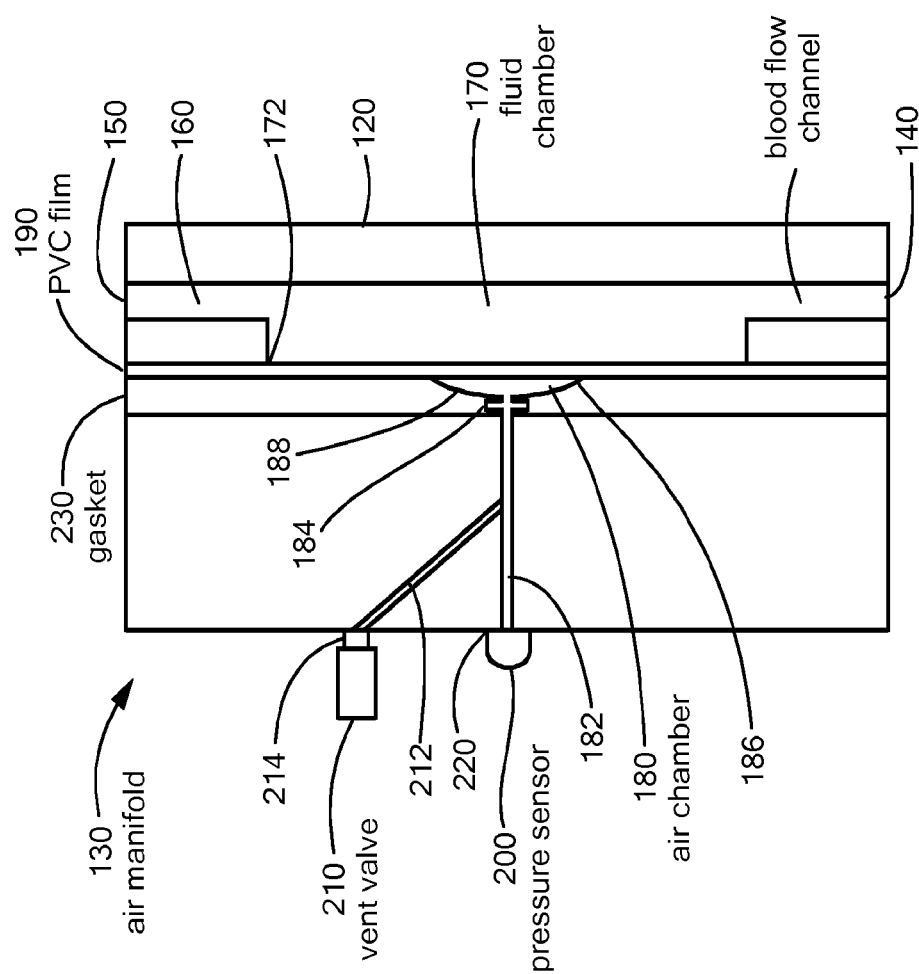
FIG. 5 schematically shows a cross-sectional view of an alternative pressure measurement device, in accordance with additional embodiments of the present invention.

Although the device described above and shown in FIGS. 2-4 only has the diaphragm 190 located between the air and fluid housings 130/120 of the device 100, as shown in FIGS. 5 and 6, other embodiments may include additional components. For example, in some embodiments, the device 100 may include a gasket 230 between the air and fluid housing 130/120. When the housings 120/130 are secured together, the gasket 230 may create a seal between the housings 120/130 to prevent air from leaking into or out of the chambers 170/180 from between the housings 120/130 (e.g., between the air manifold 130 and the diaphragm 190).

Figures 7A, 7B:
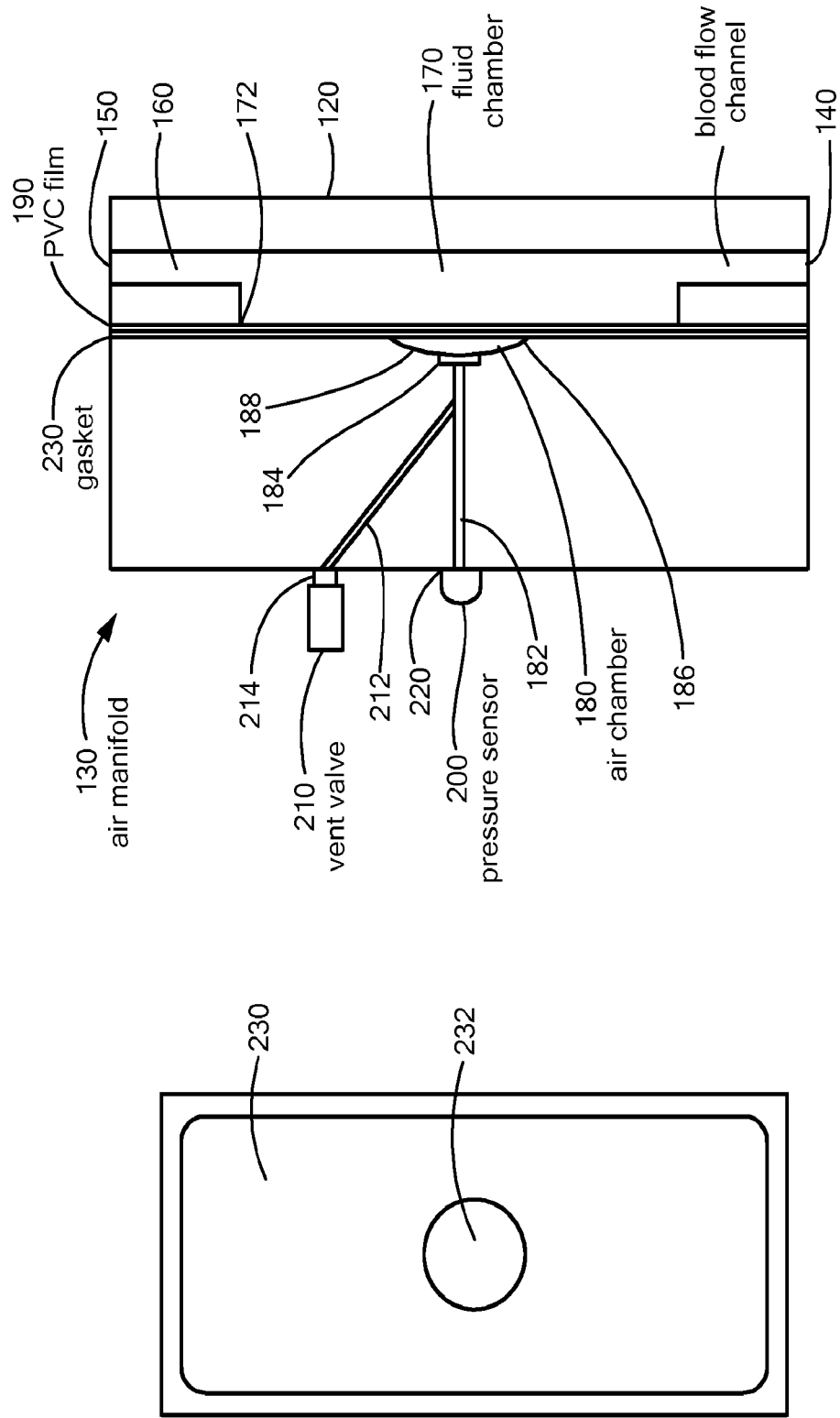
FIG. 7A schematically shows a gasket for use with the additional alternative pressure measurement device shown in FIG. 5, in accordance with further embodiments of the present invention FIG. 7B schematically shows a cross-sectional view of a pressure measurement device with an alternative gasket, in accordance with further embodiments of the present invention.
Figure 10:
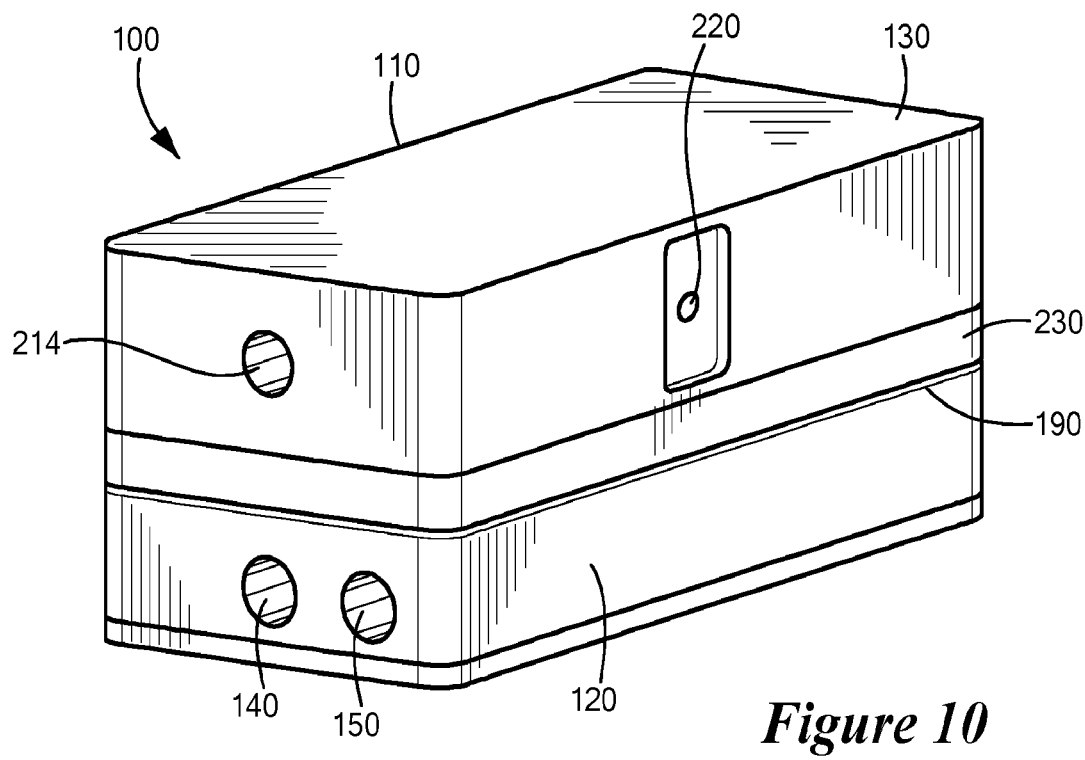
FIG. 10 schematically shows a further alternative pressure measurement device for measuring the pressure within a fluid path, in accordance with various embodiments of the present invention.

It should be noted that, in some embodiments, the gasket 230 may form at least part of the air chamber 180. For example, as best shown in FIG. 5, the air chamber 180 (e.g., with or without the recess 184) may be formed directly into the gasket 230 (e.g., as opposed to the body of the first housing 130) (FIG. 7A). Alternatively, in other embodiments, the air chamber 180 may still be formed within the first housing 130, and the gasket 230 can merely include a through-hole 232 that is sized similar to the air chamber 180. In such embodiments, the through-hole 232 in the gasket 230 may act as the opening 186 to the air chamber 180 to allow the diaphragm 190 to deform into the air chamber 180.

Alternatively, as shown in FIG. 7B, the gasket 230 may be a solid film with no through-hole. In such embodiments, the gasket 230 will deform into the air chamber 180 and the fluid chamber 170 with the diaphragm 190 (e.g., acting as part of the diaphragm 190 as the pressure within the fluid path 160 increases and decreased). In such embodiments, the plain/solid gasket 230 may be a thin flexible silicone rubber film that fully covers the air chamber opening 186 and applies no or minimal resistance to the diaphragm deformation.

The gasket 230 may be made from any number of materials including, but not limited to silicone rubber or a removable double adhesive film. For example, in embodiments in which the air chamber 180 is formed in the gasket 230, the gasket 230 may be a relatively thick silicone rubber. Alternatively, if the air chamber 180 is not formed in the gasket 230, the gasket 230 may a thin silicon rubber film. Regardless of the material and thickness chosen, the gasket material should have a non-sticky surface at the air chamber opening 186 on the air chamber 180 side (to prevent the diaphragm 190 from sticking the air chamber walls) and at the fluid chamber opening 172 on the fluid chamber 170 side where the gasket contacts the moving diaphragm 190 (to prevent the diaphragm 190 from sticking to the gasket).

In some applications, it may be beneficial to at least partially isolate the fluid chamber 190 from the fluid path 160. To that end, as shown in FIGS. 8 and 9, some embodiments of the fluid housing 120 may include a wall 132 that separates the fluid chamber 170 from the fluid path 160. The wall 132 may include one or more holes 134A/B that fluidly connect the fluid chamber 170 and the fluid path 160 and allow the pressure within the fluid path 160 to be communicated to the fluid chamber 170. It should be noted that, in some embodiments, the wall 132 and the holes 134A/B may allow the liquid flowing through the device 100 to enter the fluid chamber 170. However, in other embodiments, the holes 134A/B may be sized such that the liquid flowing through the device does not enter the fluid chamber 170.

Although the embodiments discussed above have a fluid path 160 that extends straight through the device 100 (e.g., such that the inlet 140 and outlet 150 are aligned and on opposite sides of the housing 110), other embodiments may have different fluid path configurations. For example, as shown in FIGS. 10 and 11A-11C, the fluid path 240 may my U-shaped (FIG. 11B) and the inlet 140 and outlet 150 may be located on the same side of the housing 110. In such embodiments, the fluid/liquid may enter the inlet 140, flow through the U-shaped fluid path 240 and exit the device 100 through the outlet 150 on the same side of the device 100 as the inlet 140.

Figure 11A:
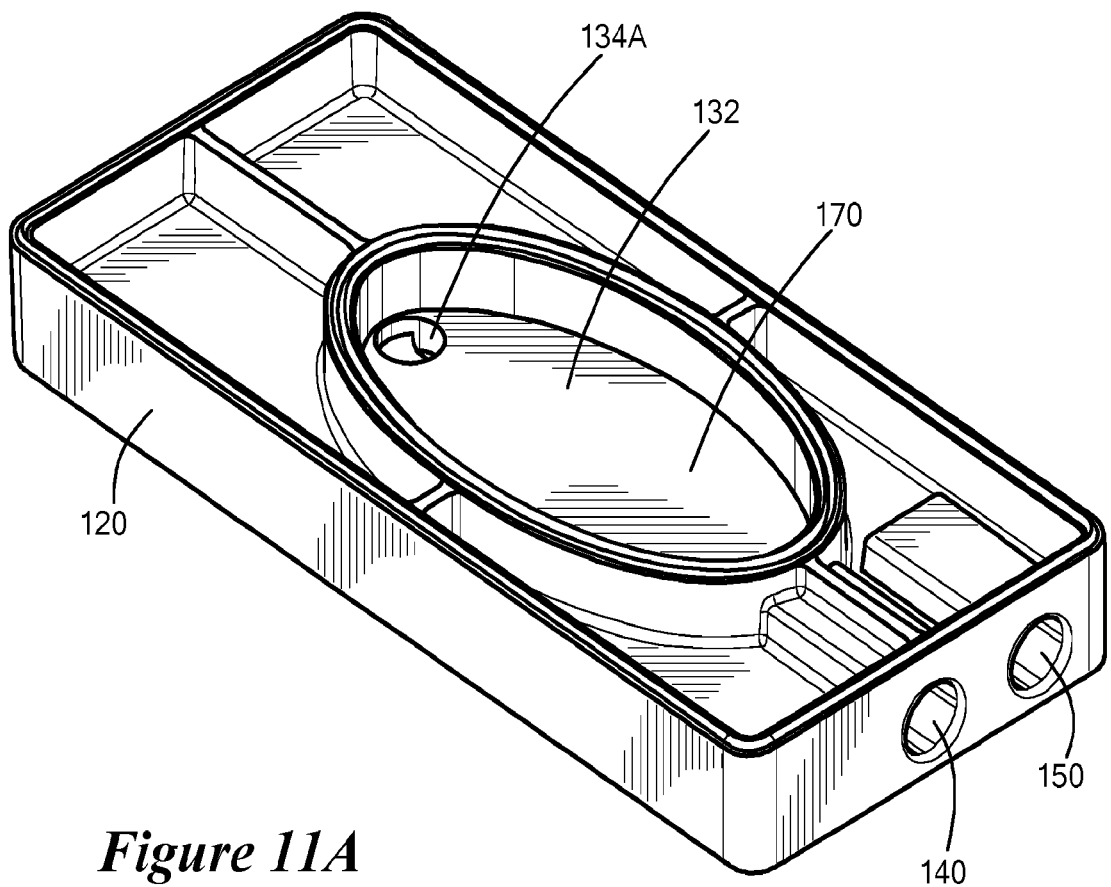
FIG. 11A schematically shows a top view of a fluid flow section of the pressure measurement device shown in FIG. 10, in accordance with some embodiments of the present invention.
Figure 11B:
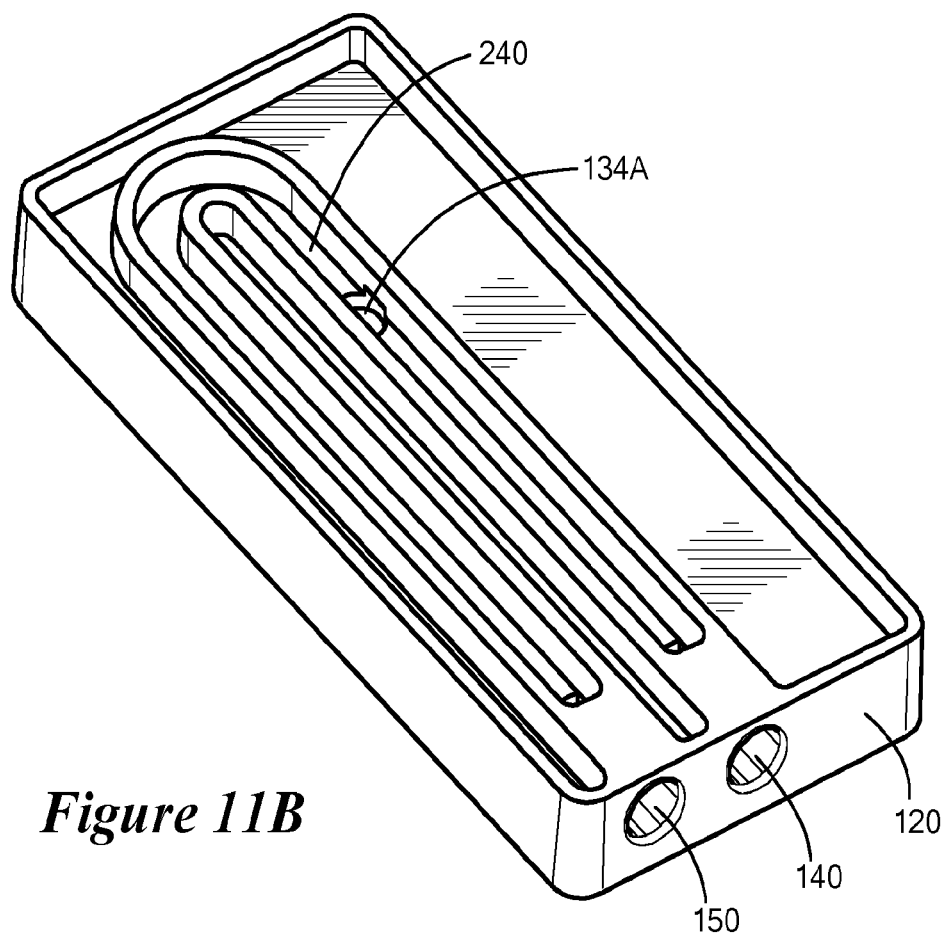
FIG. 11B schematically shows a bottom view of the fluid flow section of the pressure measurement device shown in FIG. 10, in accordance with some embodiments of the present invention.
Figure 11C:
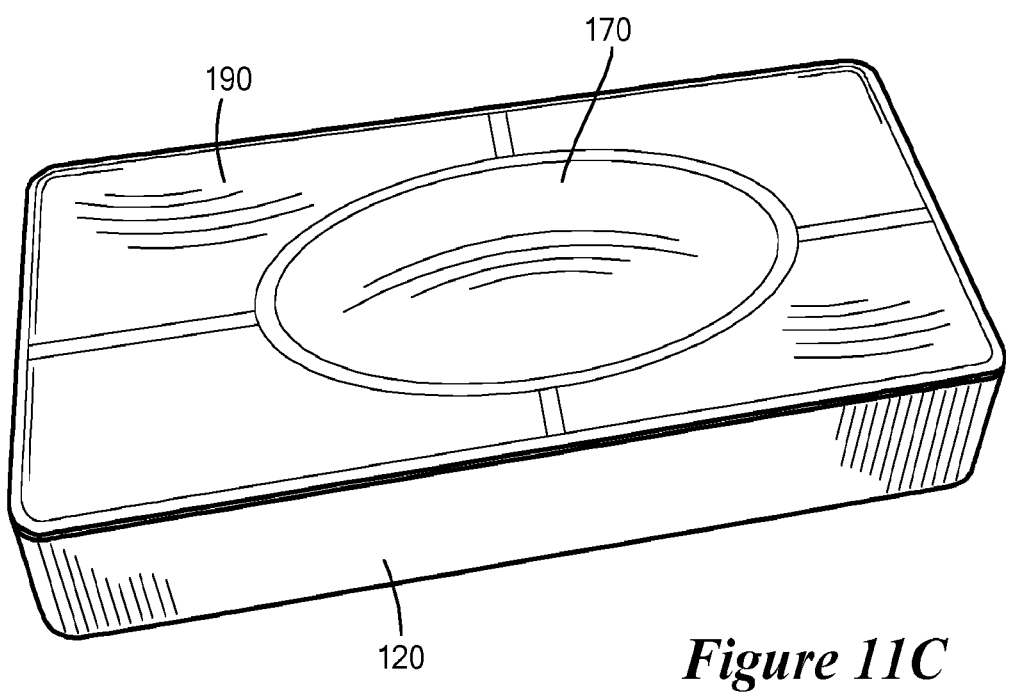
FIG. 11C schematically shows a top view of a fluid flow section of the pressure measurement device shown in FIG. 10 with the diaphragm secured, in accordance with some embodiments of the present invention.

Like the embodiments discussed above, the fluid path 240 may be in fluid communication with the fluid chamber 170. For example, as best shown in FIG. 11A, the fluid housing 120 may include a wall 132 that separates the fluid chamber 170 from the fluid path 240, and one or more holes 134A/B that allow the pressure changes within the fluid path 240 to be translated to the fluid chamber 170 (e.g., to cause the diaphragm 190 to deform as discussed above). Alternatively, the fluid chamber 170 may be in direct fluid communication with the fluid path 240 (e.g., the fluid housing 120 may not include the wall 132 in a manner similar to that shown in FIGS. 2 and 4). Also like the embodiments discussed above, the diaphragm 190 may secured to/sealed to the fluid housing 120 (FIG. 11C).

Figure 12:
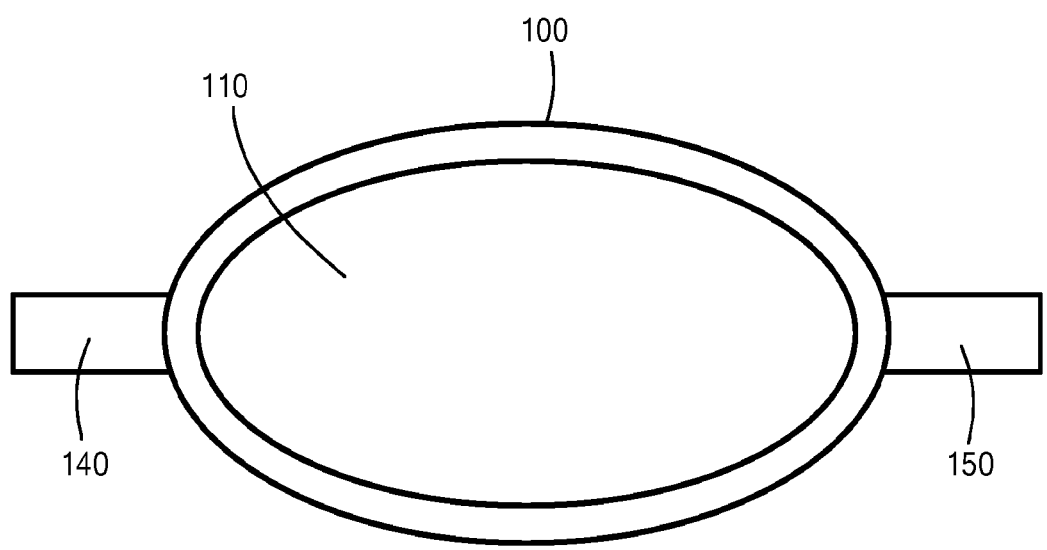
FIG. 12 schematically shows an additional alternative embodiment of a pressure measurement device in accordance with various embodiments of the present invention.

Although the figures show and the embodiments discussed above have a rectangular housing 100, other embodiments can have different housing configurations. For example, as shown in FIG. 12, the housing 100 can be oval in shape (e.g., a shape similar to the shape of the fluid chamber 170) to reduce the overall size of the device 100. Alternatively, the housing 100 may circular, square, triangular, to name but a few. In some embodiments, the shape of the fluid chamber housing 120 can differ from the shape of the air chamber housing 130. For example, the air chamber housing 130 can be rectangular, while the fluid chamber housing 120 can be elliptical. Alternatively, the air chamber housing may be elliptical and the fluid chamber housing can be rectangular.

It is important to note that, although the embodiments described above are essentially standalone devices/systems that measure the pressure within the fluid path 160, other embodiments may be incorporated into the fluid processing device. For example, if the fluid processing device is a blood processing device, the pressure sensor 200 and the air manifold 130 may be incorporated into and part of the blood processing device. In such embodiments, the user may insert the fluid housing 120 into the blood processing device to connect the air manifold 130 and the fluid housing 120, and connect tubing within the blood processing system to the inlet 140 and outlet 150 of the fluid housing 120. The user/technician may then flow the liquid (e.g., blood or blood components) through the fluid housing 120, and the pressure sensor 200 can measure the pressure within the fluid path 160 (or fluid path 240) as described above.

Exemplary Study

Different fluid chamber and air chamber sizes, membrane materials and construction methods were tested, and a 32 mm×15 mm elliptic (equivalent to 21 mm circular) fluid chamber was designed and injection molded using PVC plastics. A 0.015" (nominal 0.016") PVC membrane was ultrasonically welded to the PVC substrate, and a 12 mm circular hole was punched through a 1/16" thick silicone gasket as the main air chamber. The air manifold had a boss protruding into the circular air chamber to reduce the air volume. The total air volume was about 190 ul, including air channels in the air manifold and part of the plastic vent tubing. The parts were clamped together to form a sealed air chamber and the fluid chamber was connected to external sources, liquid and/or air.

Figure 13:
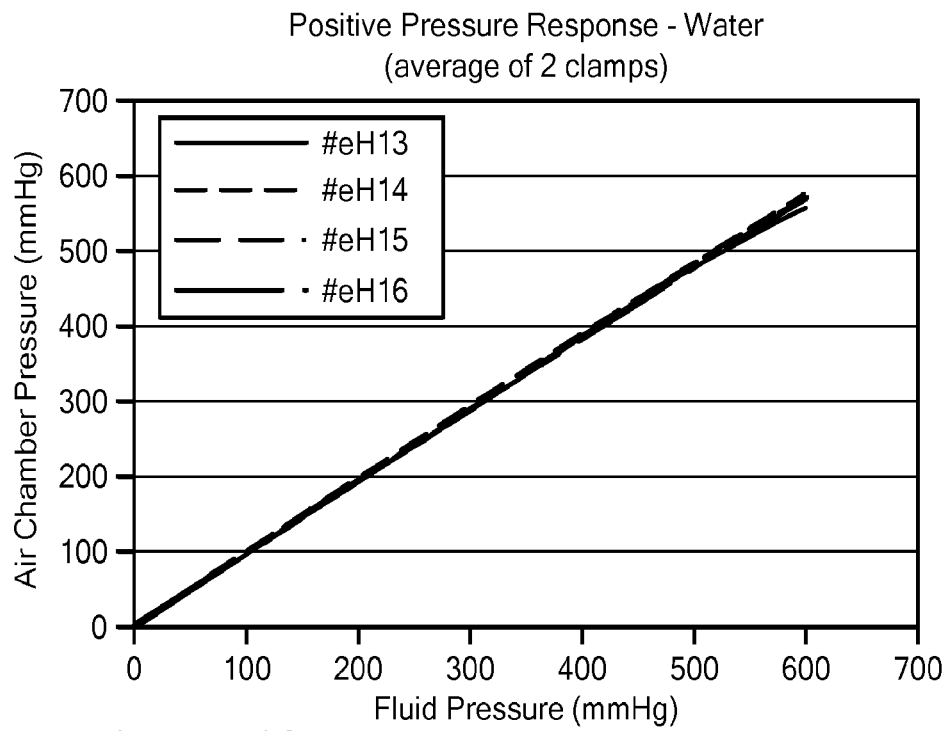
FIGS. 13 and 14 show an exemplary device's pressure response, in accordance with various embodiments of the present invention.
Figure 14:
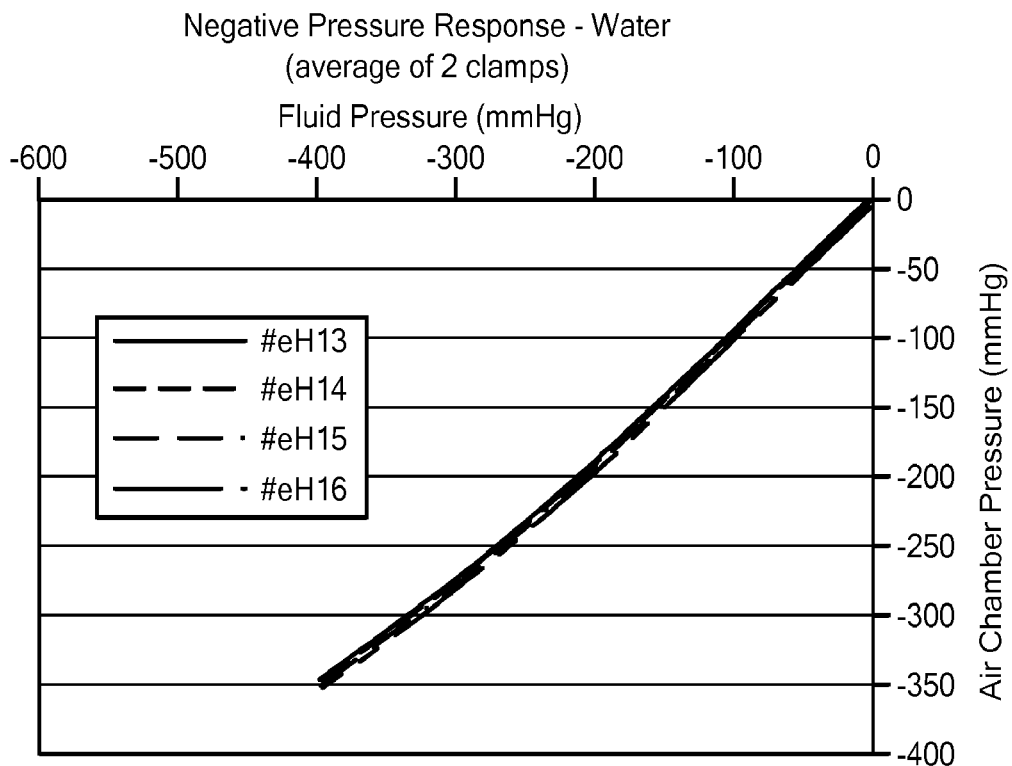
Figure 15:
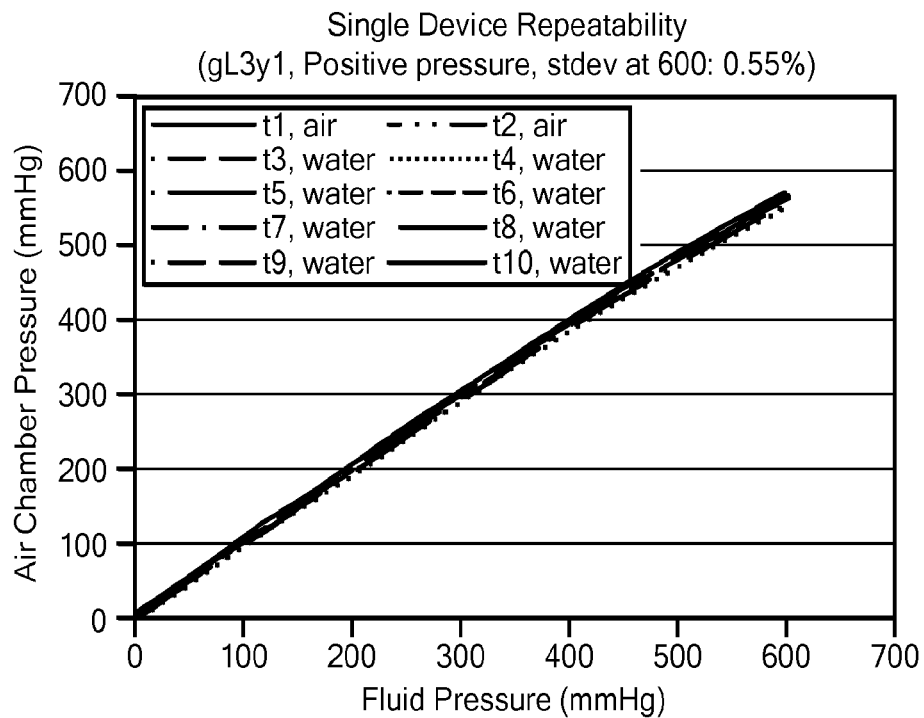
FIGS. 15 and 16 show a single exemplary device's pressure response repeatability, in accordance with some embodiments of the present invention.
Figure 16:
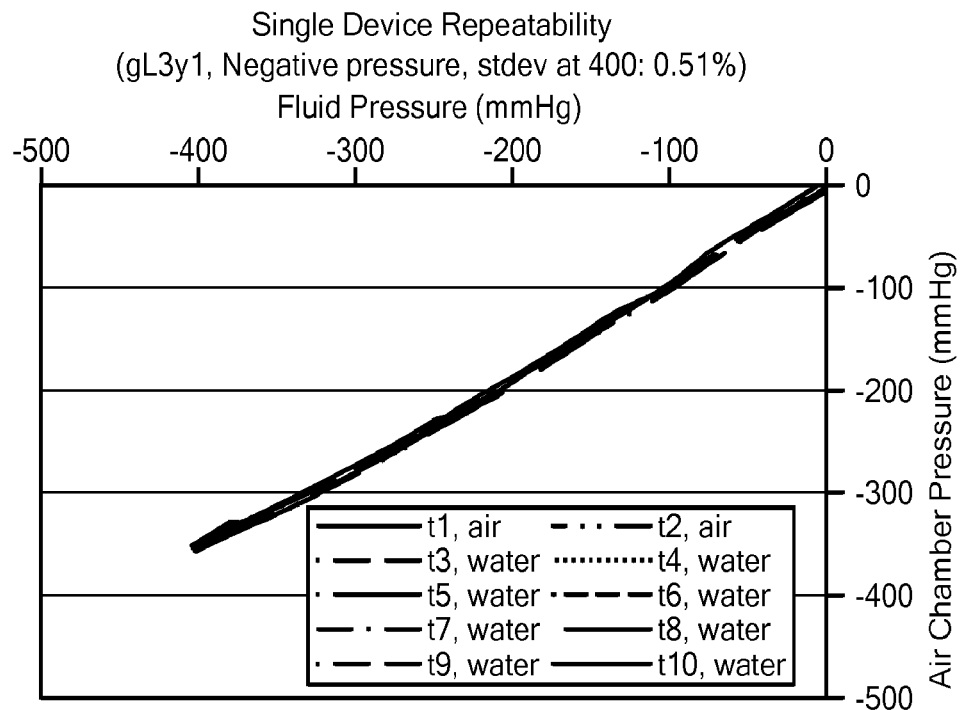
Figure 17:
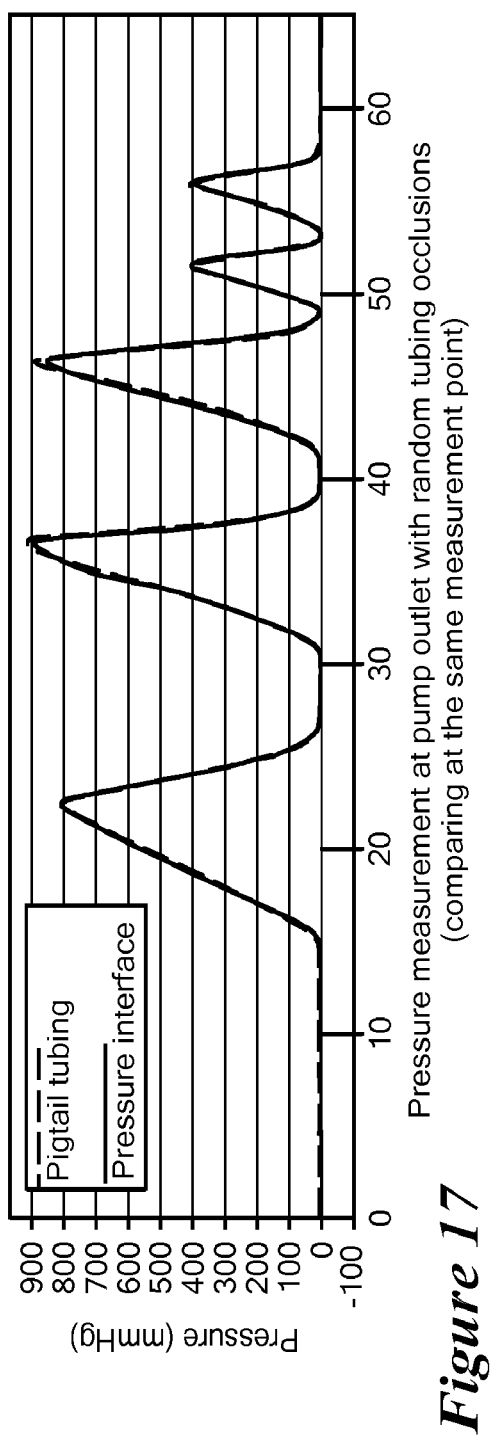
FIGS. 17 and 18 show pressure measurements at a pump's outlet and inlet, in accordance with various embodiments of the present invention.
Figure 18:
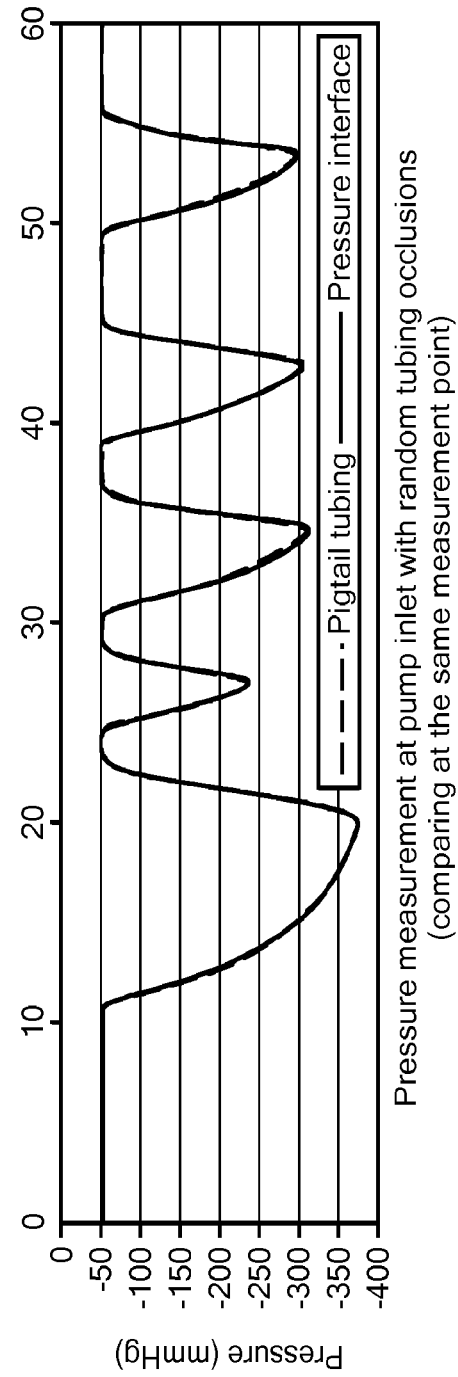

Results are shown in FIGS. 13-16. For the results shown in FIGS. 13 and 14, four individual pressure interface devices were tested together on four different clamps with the same pressure source (connected). For the results shown in FIGS. 15 and 16, a single device was repeatedly tested ten times (positive and negative tests alternatively including switch of clamps and change of fluids—water and air). Each device was tested on two clamps and the results were averaged. FIG. 13 shows the positive pressure responses of four devices and FIG. 14 shows the negative pressure responses of the same four devices. FIGS. 15 and 16 show the single device repeatability for both positive and negative responses. There was no temperature variation. The full scale errors for the results shown are about 6% for the positive pressures at 600 mmHg and 12% for the negative pressures at −400 mmHg. Since the air volume was much larger than an optimal value, the full scale errors were quite large, so a fluid pressure-air chamber pressure correlation was needed for the measurement. The response curves were very repeatable from device to device and for the single device, and also the hysteresis (pressure increases to maximum and then decreases to 0) was very small with the largest less than 1%. FIGS. 17 and 18 are the results of dynamic pump tests in comparison with prior art pigtail pressure tubing. The pressure interface device (with correlation) has very good dynamic response and accuracy, and can measure up to positive 900 mmHg and negative 400 mmHg without significant errors.

Calculating Air and Fluid Chamber Openings and Volumes

FIGS. 19A-19C illustrate an unequal diaphragm pressure sensing interface configuration, which consists of an air chamber cavity on the left and a fluid (liquid) chamber cavity on the right with a diaphragm in between. The air chamber is smaller than the fluid chamber not by the depth or cross-sectional area shown in the sketch but by the diaphragm area it covers (e.g., the interface length shown in FIGS. 19A-19C), assuming the diaphragm areas covered by both chambers are circular (shown as a line in the cross-sectional sketch) with diameters $d_a$ and $d_f$. The diaphragm is a one piece membrane covering the air chamber opening on the left and the fluid chamber opening on the right and has the same diameter as the fluid chamber opening, $d_f$, with the edge ultrasonically welded to the fluid chamber substrate or fixed using other methods. Described below is how to determine, with a given membrane material (material properties and thickness), the minimum air chamber and fluid chamber depths, maximum initial air chamber volume, and maximum initial membrane deflection or air volume variation that can be tolerated, as well as the optimal air chamber opening and fluid chamber opening sizes.

Let $V_0$ be the initial air chamber volume (including all channels and with perfectly flat diaphragm), $P_0$ be the initial air pressure and $T_0$ the initial air temperature, and assume the initial fluid (liquid) chamber pressure $P_{f0}=P_0$, which can be realized by venting both chambers to atmosphere before the fluid chamber is filled or flowing with liquid. Since a flexible plastic membrane will be used as the diaphragm, perfect diaphragm flatness is difficult to achieve even if the cross membrane pressure difference is zero. There will be always some initial membrane deformation, causing the true initial air chamber volume to deviate from its design volume $V_0$. We use $\delta V_0$ to represent this deviation, so the initial air volume is actually $V_0+\delta V_0$. Here, $\delta V_0$ can be positive and negative. After the liquid chamber is filled or flowing with liquid, the fluid chamber pressure will be $P_f$, and the air chamber pressure changes to $P_a$, volume becomes $V_a$ and temperature $T_a$. The diaphragm will be deflected toward either the air chamber or the fluid chamber depending on whether the fluid pressure $P_f$ is positive or negative. The magnitude of the deflection $f_m$ depends on the cross membrane pressure difference $\Delta P=P_a-P_f$. Based on the Ideal Gas Law, PV=nRT, where R is the gas constant and n is the air molar mass (a fixed value for a sealed volume), we have:

$$P_a V_a/T_a = nR = P_0(V_0+\delta V_0)/T_0 \qquad (1)$$

Let $\Delta T=T_a-T_0$, $\Delta V=V_a-(V_0+\delta V_0)$, and $\beta=\Delta T/T_0$, from Eq. (1), we have:

$$P_a = (1+\beta)P_0 \frac{V_0+\delta V_0}{(V_0+\delta V_0+\Delta V)} \qquad (2)$$

Here, the change of air chamber volume $\Delta V$ is caused by the diaphragm deformation under the cross membrane pressure difference $\Delta P$, i.e., $\Delta V$ is a function of $\Delta P$, $$\Delta V = f(\Delta P) \qquad (3)$$

With given $\beta$, $P_0$, $V_0$ and $\delta_0$, we still cannot solve Eq. (2) unless we know the function in Eq. (3). Since $\Delta V$ is caused by the membrane deformation, we can find $f_m$ under $\Delta P$ and then calculate $\Delta V$ from the deformed membrane geometry.

We assume the diaphragm is a circular isotropic elastic membrane with uniform thickness and diameter d, clamped at the edge, and under uniform pressure with initially flat membrane ($\delta V_0=0$). Based on Fichter's analysis (NASA Technical Paper 3658, 1997), we have the theoretical solution as follows:

The deflection of membrane at any point with radius r from the center is $$w = \frac{d}{2}\sum w_{2n}\left[1 - \left(\frac{2r}{d}\right)^{2n+2}\right], \quad n = 0, 1, 2, 3, \ldots \quad (4)$$

The maximum deflection is at the center with r=0, so $$f_m = \frac{d}{2}\sum w_{2n}, \quad n = 0, 1, 2, 3, \ldots \quad (5)$$

where the coefficients w0, w2, w4, . . . can be calculated with the following expressions, $$\begin{aligned}
w_0 &= \frac{n_0}{4} \\
w_2 &= \frac{1 + 8an_0 q}{512 n_0^4 q} \\
w_4 &= \frac{(1 + 8an_0 q)(5 + 8n_0 q + 32an_0 q)}{147456 n_0^7 q^2} \\
w_6 &= \frac{(1 + 8an_0 q)\left(\begin{array}{c}55 + 192 n_0 q + 704 an_0 q \\ + 128 n_0^2 q^2 + 1344 an_0^2 q^2 + 2176 a^2 n_0^2 q^2\end{array}\right)}{75497472 n_0^{10} q^3} \\
w_8 &= (1 + 8an_0 q)[259 + (1366 + 5030a + 288 n_0^2)n_0 q + \\
&\quad (1920 + 19008a + 31744 a^2 + 4608 n_0^2)n_0^2 q^2 + \\
&\quad (768 + 13952a + 65408 a^2 + 64512 a^3 + 36864 an_0^2 - 18432 a^2 n_0^2) \\
&\quad n_0^3 q^3]/15099494400 n_0^{13} q^4 \\
&\ldots
\end{aligned}$$

where $$a = \frac{3+\mu}{2}, \quad q = \frac{\Delta P d}{2Eh},$$

with μ is Poisson ratio, E the elastic modulus and h the thickness of the membrane; and $n_0$ is the solution of the following equation, $$\left(\frac{1-\mu}{2}\right)n_0 + \left(\frac{3-\mu}{2}\right)n_2 + \left(\frac{5-\mu}{2}\right)n_4 + \left(\frac{7-\mu}{2}\right)n_6 + \quad (7)$$
$$\left(\frac{9-\mu}{2}\right)n_8 + \ldots + w_0 + 2w_2 + 3w_4 + 4w_6 + 5w_8 + \ldots = 0$$

where $n_2$, $n_4$, $n_6$, $n_8$, . . . are related to $n_0$ by the following equations, $$\begin{aligned}
2n_0 w_2 + n_2 w_0 &= 0 \\
3n_0 w_4 + 2n_2 w_2 + n_4 w_0 &= 0 \\
4n_0 w_6 + 3n_2 w_4 + 2n_4 w_2 + n_6 w_0 &= 0 \\
5n_0 w_8 + 4n_2 w_6 + 3n_4 w_4 + 2n_6 w_2 + n_8 w_0 &= 0 \\
\ldots
\end{aligned} \quad (8)$$

Or by direct expression as:

$$\begin{aligned}
n_2 &= -\frac{(1 + 8an_0 q)}{64 n_0^2 q} \\
n_4 &= -\frac{(1 + 8an_0 q)[1 + 4n_0 q(1+a)]}{6144 n_0^5 q^2} \\
n_6 &= -\frac{(1 + 8an_0 q)\left[\begin{array}{c}13 + n_0 q(96 + 128a) + \\ 576 an_0^2 + n_0^2 q^2 (128 + 256a)\end{array}\right]}{4718592 n_0^8 q^3} \\
n_8 &= -(1 + 8an_0 q)[39 + n_0 q(366 + 670a + 288 n_0^2) + \\
&\quad n_0^2 q^2 (960 + 4608a + 3584 a^2 + 4608 n_0^2) + n_0^3 q^3 \\
&\quad (768 + 6272a + 14208 a^2 + 5632 a^3 + 36864 an^2 - 18432 a^2 n_0^2)/ \\
&\quad 754974720 n_0^{11} q^4
\end{aligned} \quad (9)$$

Substituting Eq. (6) and Eq. (9) into Eq. (7), we can solve $n_0$, so we can get the ws from Eq. (6). The membrane deflection is the summation of all ws, theoretically infinite terms. Fortunately, in general, the summation of the first five terms, $w_0$, $w_2$, $w_4$, $w_6$, $w_8$, in Eq. (5) is sufficient to represent the true deflection $f_m$. The higher number terms are very small in value and negligible. An iterative method can be used to solve the above equations.

The deformed membrane will have stress proportional to the deflection. The maximum stress occurs at the edge of the membrane, which can be estimated by the following formula, $$N = \Delta P \frac{d}{2}\sum n_{2m}, \quad m = 0, 1, 2, 3, \ldots \quad (10)$$

where $n_0$, $n_2$, $n_4$, . . . are calculated from Eq. (9). By assuming a spherical shape of the deformed membrane (actually parabolic), which is a quite accurate estimation for small membrane deflection, the air chamber volume change $\Delta V$ can be related to the membrane deflection $f_m$ through the following formula, $$\Delta V = \frac{\pi f_m}{24}(3d^2 + 4 f_m^2) \quad (11)$$

Under positive fluid pressure, the membrane deflects toward the air chamber, use $d_a$ in place of the membrane diameter d, and the $f_m$ is negative because $\Delta P$ is negative. Under negative fluid pressure, the membrane deflects toward the fluid chamber, use $d_f$ in place of d and $f_m$ is positive.

Once $\Delta V$ is known, from the maximum expected fluid pressure $P_f$ to be measured, we can calculate the maximum air chamber volume that matches the deformed membrane shape (plus a safety volume or depth $\delta f_m$). The total air volume $V_0$ can be estimated as:

$$V_0 = \frac{\Delta V}{(1+\beta)P_0/(\Delta P + P_f + P_0) - 1} + V_{ch} \quad (12)$$

where $V_{ch}$ is the air volume attributed from air channels, vent ports and other structures (the smaller the better), and the $\Delta V$ is calculated based on the maximum expected membrane deflection $f_m$+safety depth $\delta f_m$ or maximum estimated pre-deflection $f_{m0}$, whichever is larger. $P_f$ is gauge pressure and $P_0$ equals local atmospheric pressure. The $\Delta P$ required to deform the membrane to satisfy the air chamber pressure-volume relationship defines the measurement error, i.e., $$\text{Error (\%)} = \Delta P / P_f * 100 \qquad (13)$$

Examples of Pressure Interface Design

As an example, a 0.016" (0.406 mm) thick PVC membrane was chosen as the diaphragm, circular shape, with elastic modulus E=13.79 MPa, Poisson ratio 0.382, density 1.21 g/cm3. Let initial air pressure $P_0$=760 mmHg (atmospheric pressure), $T_0$=22° C.=295.15K and assume air chamber bottom is curved, matching the deformed membrane shape (smallest air volume), with a depth of 1.2 times the expected maximum air chamber membrane deflection. The target pressure measurement range is −300 mmHg to +600 mmHg (for high Hct red blood cell removal from the rotating centrifuge and returning to the donor on a centrifuge based blood apheresis instrument). To allow for fluctuations and tolerances, 100 mmHg may be added to both ends, i.e., from −400 mmHg to +700 mmHg, as the pressure sensing interface design requirement. The full scale measurement error is required to be less than 2%. Assume the portion of air volume contributed from the air channels, sensor & vent ports and other structures is fixed at $V_{ch}$=24 ul, which cannot be changed (e.g., in this example). The diameters of the air chamber opening and the fluid chamber opening, $d_a$ and $d_f$, may be determined and then based on the maximum expected membrane deflection to determine the minimum depths required for the air and fluid chambers. The total initial air volume $V_0$ is equal to the sum of the air chamber volume and the air channel volume (24 ul in this example).

In the following, the expected performance of three equal diaphragm designs ($d_f = d_a$=12.7, 25.4 and 50.8 mm) and two unequal diaphragm designs ($d_f / d_a$=25.4/12.7 and 25.4/18.0) is compared. Below demonstrates how the unequal diaphragm design is better than the equal diaphragm design in terms of performance and robustness in some applications.

With Initially Perfect Flat Diaphragm ($f_{m0}$=0),

In this example, the assumption is that everything is perfect, no initial membrane deflection, no temperature variation. When the design is capable of measuring maximum pressures (+700 mmHg or −400 mmHg), the goal is to see the accuracy the device can achieve. When the design is not able to reach maximum performance, the goal is to see how large a pressure the device can measure with a 2% full scale error. The air chamber volume is determined by the maximum membrane deflection $f_m$ under the highest positive pressure it can measure. The air chamber depth is equal to 1.2 times of $f_m$ ($\delta f_m$=20% $f_m$) to accommodate unexpected conditions.

Table I shows the predicted results. The results show that with the small air chamber opening ($d_a$=12.7 mm), the pressure interface device can measure pressures up to 550 mmHg. In order to measure 700 mmHg, the air chamber opening may be increased to at least 18 mm. The fluid chamber opening size has no effect on positive pressure measurement. However, the air chamber size has effect on the negative pressure measurement. With equal diaphragm design, the pressure interface cannot measure negative 400 mmHg when $d_a$ is 25.4 mm and less. Even when the membrane size is doubled to 50.8 mm, it can barely measure negative 400 mmHg with a full scale error 2%. While, with the unequal diaphragm design, it can easily measure negative pressure up to 400 mmHg with the smallest air chamber size 12.7 mm and with a doubled accuracy (FS error <1%). Therefore, the unequal diaphragm design described herein has significant advantages over prior art systems with equal diaphragm configurations.

TABLE I

Different pressure interface designs and their expected performance.

| | Input | | | | | Target Pressure | | Mem Defl | Air Chamber | |
|---|---|---|---|---|---|---|---|---|---|---|
| T0 22° C. | ΔT ° C. | da mm | df mm | fm0 mm | δV0 ul | Pf mmHg | FS Error % | fm mm | depth mm | Vol ul |
| Equal diaphragm | 0 | 12.7 | 12.7 | 0 | 0 | 550 | 2 | 0.314 | 0.377 | 47.89 |
| | | | | 0 | 0 | −150 | 2 | 0.183 | | |
| | | 25.4 | 25.4 | 0 | 0 | 700 | 0.5 | 0.520 | 0.625 | 182.37 |
| | | | | 0 | 0 | −380 | 2 | 0.718 | | |
| | | 50.8 | 50.8 | 0 | 0 | 700 | 0.5 | 1.387 | 1.665 | 1713.6 |
| | | | | 0 | 0 | −400 | 2 | 1.946 | | |
| Unequal Diaphragm | 0 | 12.7 | 25.4 | 0 | 0 | 550 | 2 | 0.314 | 0.377 | 47.89 |
| | | | | 0 | 0 | −400 | 1 | 0.550 | | |
| | | 18 | 25.4 | 0 | 0 | 700 | 0.5 | 0.319 | 0.383 | 72.81 |
| | | | | 0 | 0 | −400 | 1 | 0.550 | | |

Effect of Initial Membrane Deflection and Temperature Variations:

In the above example, a perfectly flat initial membrane condition was assumed (e.g., $\delta V_0$=0 was assumed—which may be hard to achieve in practice). When $\delta V_0 \neq 0$, (e.g., the membrane is pre-deflected by an amount $f_{m0}$) the pressure measurement accuracy will be affected. If the membrane pre-deflects toward the air chamber ($\delta V_0 < 0$), intuitively, one may expect a better performance because the air volume is smaller so that a higher pressure can be measured based on the Ideal Gas Law, however, on the contrary, the positive pressure measurement accuracy will drop because higher cross-membrane pressure difference is required for the increased membrane deformation, meaning a lower air pressure reading $P_a$ for the same input fluid pressure $P_f$. However, it is beneficial for the negative pressure measurement because less final membrane deformation is required for the same $P_f$. On the other hand, if the membrane pre-deflects toward the fluid chamber ($\delta V_0 > 0$), it will benefit positive pressure measurement but not negative pressure measurement.

For robust device design, the pressure interface should be able to tolerate a non-flat initial membrane condition. For worst case scenarios, a negative $\delta V_0$ for positive pressure measurement and positive $\delta V_0$ for negative pressure measurement should be considered. For fair comparison, the initial deflection value is set, for all cases, equivalent to that caused by a 0.5 mmHg cross-membrane pressure difference in the following calculations.

At the same time, the pressure interface performance will be affected by temperature variations based on the Ideal Gas Law. In some practical applications, the fluid temperature may vary. For example, blood drawn from the donor has a temperature close to the body temperature (~37° C.) initially and cools down during processing at room temperature (about 22° C.). Also, some reagents or stored blood may have a temperature below room temperature when they are taken from the refrigerator (~8° C.). When the system is calibrated and started at room temperature, the fluid temperature changes will affect the air pressure measurement. In general, a decreased temperature will decrease the accuracy of positive pressure measurement but benefit the negative pressure measurement; while an increased temperature will decrease the accuracy of negative pressure measurement but benefit the positive pressure measurement. In order to design a device able to tolerate temperature variations, a temperature drop of 14° C. (22° C.–8° C.) for the positive pressure measurement and a temperature increase of 15° C. (37° C.–22° C.) for negative pressure measurement may be considered as worst case scenarios to test the tolerance of different interface designs.

The non-flat membrane condition and temperature variation may be combined together in the analyses. The results are shown in Table II. The results show that the initial membrane deflection and temperature variation have dramatic effects on the negative pressure measurement of all equal diaphragm designs, making them unworkable, but only slight effects on the negative pressure measurement of both unequal diaphragm designs, only suffering a little reduction on the measurement accuracy (still less than 2%). For the positive pressure measurement, the effects are the same for equal and unequal diaphragm designs. From these results, it can be seen that the equal diaphragm designs are not able to tolerate any membrane or temperature variations while the unequal diaphragm designs can. This is a significant advantage of the unequal diaphragm designs. With the unequal diaphragm design, it is possible to develop a robust pressure sensing interface device that can tolerate certain membrane condition changes including material property changes and operation environmental condition variations such as temperature and operation errors as long as the deviations are not too large.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An apparatus for measuring pressure within a fluid path, the apparatus comprising:
   a first housing portion defining a structure of the apparatus and having a fluid path extending through the first housing portion, the fluid path configured to allow a liquid to pass through the first housing portion from an inlet port to an outlet port, each of the inlet port and the outlet port being defined by the first housing portion;
   a first volume chamber in fluid communication with the fluid path and having a first volume chamber opening, the first volume chamber being defined by the first housing portion;
   a second housing portion;
   a second volume chamber having a second volume chamber opening, the second volume chamber opening being smaller than the first volume chamber opening, the second volume chamber being defined by a wall of the second housing portion;
   a diaphragm separating the first volume chamber from the second volume chamber and fluidly disconnecting the second volume chamber from the fluid path, such that the fluid path does not pass through the diaphragm and does not pass through the second housing portion, the diaphragm configured to deform based upon the pressure within the fluid path;
   a pressure-measurement port defined by the second housing portion and located in the wall of the second volume chamber spaced from the diaphragm so as avoid being blocked by the diaphragm as it extends into the second chamber; and
   a pressure sensor for providing a pressure measurement, the pressure sensor being in fluid communication with the second volume chamber through the pressure-measurement port, so that the pressure sensor is spaced away from the diaphragm separating the first volume chamber from the second volume chamber;
   wherein the first volume chamber opening and the second volume chamber opening face each other and are adjacent to each other across the diaphragm;

TABLE II

Expected performance of different pressure interface designs under the effects of initial membrane deflection and temperature change.

| | Input | | | | | Target Pressure | | Mem Defl | Air Chamber | |
|---|---|---|---|---|---|---|---|---|---|---|
| T0 22° C. | ΔT ° C. | da mm | df mm | fm0 mm | δ V0 ul | Pf mmHg | FS Error % | fm mm | depth mm | Vol ul |
| Equal diaphragm | −14 | 12.7 | 12.7 | −0.086 | −5.45 | 200 | 2.90 | 0.154 | 0.240 | 39.20 |
| | 15 | | | 0.086 | 5.45 | −70 | 4.43 | 0.099 | | |
| | −14 | 25.4 | 25.4 | −0.23 | −58.28 | 700 | 1.20 | 0.520 | 0.750 | 214.36 |
| | 15 | | | 0.23 | 58.28 | −240 | 2.75 | 0.445 | | |
| | −14 | 50.8 | 50.8 | −0.616 | −624.39 | 700 | 1.23 | 1.387 | 2.003 | 2058.5 |
| | 15 | | | 0.616 | 624.39 | −260 | 2.69 | 1.227 | | |
| Unequal Diaphragm | −14 | 12.7 | 25.4 | −0.086 | −5.45 | 200 | 2.90 | 0.154 | 0.240 | 39.20 |
| | 15 | | | 0.23 | 58.28 | −400 | 1.45 | 0.412 | | |
| | −14 | 18 | 25.4 | −0.141 | −17.94 | 700 | 1.50 | 0.368 | 0.509 | 88.78 |
| | 15 | | | 0.23 | 58.28 | −400 | 1.80 | 0.474 | | | wherein the second volume chamber opening is smaller than the first volume chamber opening such that a ratio of the size of the second volume chamber opening to the first volume chamber opening is between 1.4:1 and 100:1, so as to reduce the effect of material property changes in the diaphragm and operation environmental condition variations on the pressure measurement.

2. An apparatus according to claim 1, wherein the first housing portion is disposable and configured to be disconnected from the second housing portion, while the second housing portion is configured to be reused.

3. An apparatus according to claim 1, further comprising a gasket extending between the first and second housing portions, the gasket configured to prevent air leakage when the first and second housing portions are coupled.

4. An apparatus according to claim 3, wherein the gasket includes an opening therethrough, the opening defining at least a portion of the second volume chamber.

5. An apparatus according to claim 1, wherein the diaphragm is ultrasonically welded to the first housing portion, thereby sealing the first volume chamber.

6. An apparatus according to claim 1, wherein the second housing portion includes a vent port in fluid communication with the second volume chamber via a vent channel, the vent port and vent channel configured to allow the second volume chamber to vent as the diaphragm deforms.

7. An apparatus according to claim 6, further comprising a vent valve located on the vent port.

8. An apparatus according to claim 1, wherein the diaphragm is configured to deform into the second volume chamber if the pressure within the fluid path is positive.

9. An apparatus according to claim 1, wherein the diaphragm is configured to deform into the first volume chamber if the pressure within the fluid path is negative.

10. An apparatus according to claim 1, wherein the wall of the second volume chamber has a curved surface, the diaphragm configured to deform to the curved surface at a maximum pressure within the fluid path.

11. An apparatus according to claim 1, wherein the first volume chamber includes a first volume and the second volume chamber includes a second volume, the second volume being less than the first volume.

12. An apparatus according to claim 1 wherein a ratio of the size of the second volume chamber opening to the first volume chamber opening is between 4:1 and 9:1.

13. An apparatus according to claim 1, wherein the second volume chamber is an air chamber.

14. A method for monitoring pressure within a fluid path, the method comprising:
fluidly connecting a pressure monitoring device to a fluid flow system, the pressure monitoring device comprising:
a first housing portion defining a structure of the pressure monitoring device and having a fluid path extending through the first housing portion, the fluid path configured to allow a liquid to pass through the first housing portion from an inlet port to an outlet port, each of the inlet port and the outlet port being defined by the first housing portion,
a first volume chamber in fluid communication with the fluid path and having a first volume chamber opening, the first volume chamber being defined by the first housing portion,
a second housing portion,
a second volume chamber having a second volume chamber opening, the second volume chamber opening being smaller than the first volume chamber opening, the second volume chamber being defined by a wall of the second housing portion,
a diaphragm separating the first volume chamber from the second volume chamber and fluidly disconnecting the second volume chamber from the fluid path, such that the fluid path does not pass through the diaphragm and does not pass through the second housing portion,
a pressure-measurement port defined by the second housing portion and located in the wall of the second volume chamber spaced from the diaphragm so as avoid being blocked by the diaphragm extending into the second chamber, and
a pressure sensor for providing a pressure measurement, the pressure sensor being in fluid communication with the second volume chamber through the pressure-measurement port, so that the pressure sensor is spaced away from the diaphragm separating the first volume chamber from the second volume chamber;
wherein the first volume chamber opening and the second volume chamber opening face each other and are adjacent to each other across the diaphragm, and wherein the second volume chamber opening is smaller than the first volume chamber opening such that a ratio of the size of the second volume chamber opening to the first volume chamber opening is between 1.4:1 and 100:1, so as to reduce the effect of material property changes in the diaphragm and operation environmental condition variations on the pressure measurement;
flowing a fluid through the pressure monitoring device via the fluid path, thereby creating a pressure within the fluid path, a negative pressure within the fluid path causing the diaphragm to deform into the first volume chamber, a positive pressure within the fluid path causing the diaphragm to deform into the second volume chamber and compress the second volume; and
measuring the pressure within the fluid path using a pressure monitoring device, the pressure within the fluid path being a function of an amount of compression or expansion of the second volume.

15. A method according to claim 14, wherein the first housing portion is disposable and configured to be disconnected from the second housing portion, while the second housing portion is configured to be reused.

16. A method according to claim 14, further comprising a gasket extending between the first and second housing portions, the gasket configured to prevent air leakage when the first and second housing portions are coupled.

17. A method according to claim 16, wherein the gasket includes an opening therethrough, the opening defining at least a portion of the second volume chamber.

18. A method according to claim 14, wherein the diaphragm is ultrasonically welded to the first housing portion.

19. A method according to claim 14, wherein the second housing portion includes a vent port in fluid communication with the second volume chamber via a vent channel, the vent port and vent channel configured to allow the second volume chamber to vent as the diaphragm deforms.

20. A method according to claim 19, further comprising a vent valve located on the vent port.

21. A method according to claim 14, wherein the wall of the second volume chamber has a curved surface, the diaphragm configured to deform to the curved surface at a maximum pressure within the fluid path.

22. A method according to claim 14 wherein the first volume chamber has a first volume and the second volume chamber has a second volume, the second volume being less than the first volume.

23. A method according to claim 14, wherein the first volume chamber is a liquid chamber, the first volume configured to fill with liquid passing through the fluid path.

24. A method according to claim 14, wherein the second volume chamber is an air chamber.

25. A method according to claim 14, wherein the fluid flow system is a blood processing device.

* * * * *